United States Patent [19]
Schweber

[11] Patent Number: 4,983,044
[45] Date of Patent: Jan. 8, 1991

[54] QUANTITATIVE ANALYSIS OF BIOLOGICAL MATERIALS AND PHOTOGRTAPHIC FILM AND APPARATUS THEREFOR

[75] Inventor: Miriam Schweber, Lexington, Mass.

[73] Assignee: The Trustees of Boston University, Boston, Mass.

[21] Appl. No.: 32,743

[22] Filed: Mar. 31, 1987

[51] Int. Cl.$^5$ ............................................. G01N 21/59
[52] U.S. Cl. ..................................... 356/443; 356/243
[58] Field of Search ........................ 356/443, 444, 243; 354/20

[56] References Cited

U.S. PATENT DOCUMENTS

| | | | |
|---|---|---|---|
| 3,677,150 | 7/1972 | Sanford | 356/443 |
| 3,841,763 | 10/1974 | Lewis | 356/443 |
| 4,199,252 | 4/1980 | Vermeulen | 356/443 |
| 4,211,558 | 7/1980 | Oguchi et al. | 354/20 |
| 4,249,825 | 2/1981 | Shapiro | 356/223 |

OTHER PUBLICATIONS

Williams, A. T., "Densitometers and Their Use in Technology, Medicine and Commerce," *Weston Engineering Notes*, vol. 4, No. 4 (Jul. 1949), pp. 1–4 (Weston Electrical Instrument Corp.).
Devine, E. et al., *Ann. N.Y. Acad. Sci.*, 450:85–94 (1985).
Junien, C. et al., *Am. J. Human Genetics*, 35, 584–591 (1983).
Shows, T. B. et al., *Adv. Human Genetics*, 12:349 (1982).
Schweber, M., *Annals N.Y. Acad. Sci.*, 450:223 (1985).

*Primary Examiner*—Richard A. Rosenberger
*Attorney, Agent, or Firm*—Hamilton, Brook, Smith & Reynolds

[57] ABSTRACT

Accurate quantitative determination of signals produced on film by biological molecules of interest, such as DNA and RNA, identified by hybridization with radioactively-labeled probes comprising homologous sequences (DNA or RNA) is assured by means of preimaging of a density gradient reference series on the film to calibrate the linear range of the film's response. The reference may include a gradient of incremented density levels or it may include multiple steps produced by differing amounts of a standard radiant material. The film may be preimaged with a step-wedge density gradient by means of a film holder with arrangements to optically isolate a substantial portion of the film. Densitometric tracings of the signals generated by the radioactively-identified molecules can be adjusted to lie within the linear range of response of the film defined by the tracing of the step-wedge image by adjustment of the film exposure or sample concentrations.

Accurate quantitation can be assured if the heights of the peaks on the densitometric tracings of bands on the film produced by hybridization of probes containing sequences from test and reference chromosomes lie within the linear range of response of the film. Computation of the ratios of areas of test and reference sequences on each sample can then be compared to those of samples of known genetic constitution under similar conditions.

The method described can be used to detect alterations (changes from normal) in DNA content of cells within individual samples by single tracings. It can thus be used to diagnose, prenatally or postnatally, any genetic conditions, (including those such as Down Syndrome and Alzheimer's Disease), whose basis involves an abnormal quantity of DNA in cells.

8 Claims, 11 Drawing Sheets

QUANTITATIVE ANALYSIS OF BIOLOGICAL MATERIALS AND PHOTOGRTAPHIC FILM AND APPARATUS THEREFOR

FUNDING

Work described herein received funding from the Alzheimer's Disease and Related Disorders Association and the Retirement Research Foundation.

BACKGROUND

The techniques developed under the category of recombinant DNA (RDNA) technology have proven to be very powerful for molecular investigations (e.g., study of the molecular bases or mechanisms of cellular function). They are most often used for qualitative analysis.

Many important genetic conditions involve quantitative changes in the amount of DNA present in cells; these are not accompanied by related qualitative alterations (such as changes in the type of cellular proteins). Presently-available RDNA methods, however, are not useful for assessing such quantitative changes in cells on an individual basis for diagnosis or exploration of genetic conditions whose causality is unknown.

In standard RDNA methods, DNA molecules are enzymatically digested to produce small fragments; the resulting fragments are separated by size on a gel, through application of an electric field. They are subsequently transferred to a support through a procedure called blotting. Specific fragments of interest can be detected through use of a defined nucleic acid segment which has a sequence homologous to that of the fragment of interest and which has been labelled in a manner which makes it identifiable. Such segments, when inserted into a vector, are referred to as probes and are often labelled radioactively (e.g., by substitution of some of their phosphorous atoms by radioactive isotopes). When the labelled probes are combined under appropriate conditions with sample DNA (i.e., DNA to be analyzed) they will complex or hybridize with a DNA fragment which has a homologous sequence, resulting in formation of a "hybrid" molecule which is radioactive (i.e., radioactively labelled). Localization of the hybrid is detected by allowing the decay product from the radioactivity to interact with a closely-applied piece of X-ray film. When the film is developed, the silver grains that have been deposited by the beta decay energization produce a dark image on the film. The same approach can be used for RNA. Maniatis, T. et al., *Molecular Cloning: A Laboratory Approach*, Cold Spring Harbor Laboratory Press (1982).

The amount of radioactivity emitted at the point of attachment of a specific probe can be measured by determination of the density of the image created on the film in a given period of time. This then permits a measure of the amount of substance to which the radioactively labelled probe was attached. This technique can be used in principle to measure the quantity of a nucleic acid of interest in a given sample and has been employed for estimates of relative amounts of DNA and RNA in many systems. However, such techniques have methodological limitations which mean that they are not useful in investigations or diagnostic assessments which require accurate measurement of quantitative changes for individual samples.

Current models of genetic disorders, such as that for sickle cell anemia, include mutational events at the DNA level, which result in the transcription of an altered RNA and ultimate translation into an abnormal protein which, in turn, results in a disease state. However, there are many, varied genetic abnormalities which involve only quantitative changes in DNA present in cells and no identifiable mutational event, altered RNA, or abnormal protein production. Some of these are classed as chromosomal abnormalities; examples of these are Down Syndrome and several sex chromosome imbalances, such as Klinefelter's Syndrome and Turner's Syndrome.

Down Syndrome has been shown to involve an increase in relative amounts of a specific segment of chromosome 21. Down Syndrome occurs most commonly in the form of Trisomy 21. Normal cells have 2 complete chromosome 21's per cell nucleus; in Trisomy 21, cells have 3 complete chromosome 21's. The full effect of Down Syndrome has been shown to require triplication of only a limited portion of chromosome 21, which has been localized to chromosome band 21q22. When Trisomy 21 occurs, it can be detected microscopically, thus making diagnosis possible by karyotypic analysis. When Down Syndrome is caused by replication of a limited portion of chromosome 21, it is often difficult to detect karyotypically, even with intense and specialized staining examinations. Prenatal samples to be analyzed using presently-available methods are obtained through amniocentesis, a procedure which has a number of drawbacks. For example, the procedure cannot generally be carried out until the sixteenth week of pregnancy; cell culture and analysis of the fluid obtained requires three to four weeks; a 10% failure rate occurs, which requires drawing a new sample and an additional 3–4 weeks to culture the cells. In addition, there is a certain rate of incorrect diagnosis (5 per 1000 cases). Milunsky, A., *Prenatal Diagnosis of Hereditary Disorders* (2nd ed.) Charles Thomas Press, Springfield, Ill., (1979); Hirschhorn, K., In: *Methods in Cell Biology*, Latt, S. and G. Darlington (ed.), 26: 1–9 (1982).

There have been a number of attempts previously at adapting RDNA methods for the diagnosis of Down Syndrome, but each has not succeeded. The difficulties involved are exemplified in the following results of one such effort. Devine, E. et al., *Annals of the New York Academy of Sciences*, 450: 69–83 (1985).

TABLE 1

Quantitation of Hybridization to Normal and Trisomy 21 DNA

|  | $\beta$-Globin DNA | 21 Fragment | Ratio of 21 DNA/ $\beta$-Globin DNA |
|---|---|---|---|
| Trisomy 21 | 633 | 364 | .575 |
|  | 558 | 132 | .240 |
|  | 546 | 102 | .190 |
|  | 528 | 180 | .340 |
|  | 790 | 520 | .660 |
|  |  |  | 2.005 |
| Normal | 438 | 130 | .300 |
|  | 975 | 238 | .240 |
|  | 460 | 143 | .310 |
|  | 507 | 108 | .200 |
|  | 986 | 238 | .240 |
|  |  |  | 1.290 |

Combined Trisomy/Normal = 1.55

In this case, the important methodological problem was the lack of ability to control the exposure of the film to the radioactive signal. As a result, individual measurements varied widely. As shown in Table 1, overlap occurs in individual results, between normal and Down Syndrome individuals, despite the fact it was known that the DNA amounts differed because of the chromosomal analyses. To overcome this variability, multiple sample results were pooled. The same approach has been used by others in attempts to quantify DNA amounts in Down Syndrome.

RDNA quantification was reported for Cat Eye syndrome. McDermid H., et al., *Science*, 232: 646-648, (1986). However, multiple tests (9×) were done for each determination of the ratio of test chromosome to reference chromosome. The pooled mean ratio from the normal individuals was then normalized for comparison with pooled repeats of the affected people. However, pooled results cannot form the basis of a diagnostic test, which must be reliable at an individual level. Pooling of results assumes that the variability of results found upon multiple measurements will approximate a true mean value (i.e., that repeated data are subject to random variability). There is no evidence in support of this.

The variability in multiple measurements reported occurs because of the lack of control of the signal deposited on the film. Presently, however, there is no method to determine whether the image was over- or underexposed. Either produces uncontrolled results which are not expected to vary randomly. It is generally assumed that RDNA methods cannot be used for diagnosis of Down Syndrome or other conditions whose biochemical basis is a quantity of DNA present in cells of affected individuals.

In the method illustrated in simplified form in FIG. 1, DNA 22 is isolated from a tissue sample and purified. As represented in FIG. 1A, in which chromosome 21 is shown, DNA is made of pairs of strands 24, 26, which form a helical configuration; each strand of DNA is made of nucleotides 28, whose ordering in each molecule of DNA forms a specific sequence. Restriction enzymes act on specific small sequences in DNA and can be used to cut DNA, as shown in FIG. 1B. If properly-chosen restriction enzymes are used, the DNA of chromosome 21 will be cut so as to produce a number of DNA fragments originating from band 21q22.

The DNA fragments resulting from the action of (i.e., digestion by) restriction enzymes are separated on the basis of size by immersion in a gel 30 and application of an electric field as represented in FIG. 1C. As shown in FIG. 1D, the molecules are transferred to a support 32, without modifying their relative locations on the gel. The DNA molecules, immobilized on the support, are treated to separate them into their constituent strands. Cloned recombinant plasmids 36 are prepared, using known techniques; such clones contain copies of DNA fragments identified as originating from band 21q22 inserted into a vector. The cloned DNA fragments and their vectors are radioactively labelled and can be used as labelled probes which will hybridize to the DNA 34 (shown attached to support 32 in FIG. 1E) whose separated strands have a nucleotide sequence complementary to the strands of the inserted probe sequence. As a result of hybridization of a strand of probe DNA 36 with the complementary nucleotide sequences on a strand of the genomic DNA on the support 32, the homologous sequences of interest become identified. This approach has serious inherent difficulties for quantitation, however, because of the exquisite sensitivity of detection (in the nanogram range) it makes possible. It is very difficult to compare the amount of label attached to two different samples because the variation introduced in loading the samples onto the gel will often be greater than the difference being evaluated.

As represented in FIG. 1F, in standard methods, an image 40 from a radioactively labelled DNA probe attached to a genomic DNA fragment on a blot is created by exposure of an X-ray film 38 to the support. A densitometric tracing is then made of the developed film. If the exposure can be controlled, the area subsumed under the peaks of the tracing can be directly proportional to the amount of radioactivity present in the probes hybridized to DNA fragments (attached to the support) which contain homologous sequences. The amount of radioactivity deposited on the film is a direct measure of the quantity of DNA present in the sample with controlled exposure.

A critical problem exists because of the inherent non-linearity of the film response relative to exposure (known as the H-D curve in classical optics). As illustrated by FIG. 2, the film registers a linear response only in a central range of exposures. Below or above that range of exposures, the images deposited on the film are not linearly related to the signal. In those cases, the quantity of material generating the radioactive signal cannot be directly measured. Complex computer calculations based on the densitometer readings have been attempted in an effort to assure that measurements are made in the linear range of the film response. However, those calculations have not been satisfactory.

In spite of the fact that recombinant DNA technology has been available for over ten years and the optimistic predictions of its applicability to diagnosis of genetic diseases, it has had no direct application for quantitatively-based conditions. This is due to the problem described above, the lack of a sufficiently sensitive and reliable method for quantification of changes in samples at the DNA molecular level. Such a quantitative approach would be very useful in diagnosing genetic disorders in which there is an alteration in quantity of DNA and could be valuable in exploring genetic conditions whose basis is not understood. For most genetic disorders, there is no specific genetic or biochemical characterization available.

Development of such an approach would be of particularly great value in a medical and public health context in that it would make it possible to diagnose, both prenatally and postnatally, conditions whose genetic basis lies in a quantitative change in the amount of DNA (or RNA) present in cells.

DISCLOSURE OF THE INVENTION

The present invention relates to a method of quantifying nucleic acid sequences (e.g., DNA, RNA) and other biological materials in a sample, as well as to a device for use in the method.

In accordance with principles of the present invention, a photographic film holder for recording images suitable for densitometric analysis is prepared with the inclusion of an image of a densitometric reference step-wedge. The reference step-wedge includes a plurality of image regions of different densities which have a predetermined relationship to each other. Densitometric tracing directly of the reference regions forms a gradient of incremented density steps, from 0 to 100% absorbance.

When film is inserted into the holder, the step-wedge is imaged onto the film by exposure to sensitizing radiation in a manner that leaves the remainder of the film unexposed. When this is done, a densitometric tracing of the resultant film image of the step-wedge produces an S-shaped curve because only a few of the steps will have absorbancies that lie within the linear range of response of the film. Steps with too little density produce relative underexposure; those with too much produce relative overexposure. Direct measure of quantity can only be obtained by images whose densities lie within the linear area of response of the film. The image of the step-wedge can be adjusted so that the linear range of response of the film which it defines occurs in the central area of the absorbancy scale. When another section of the film is exposed to a source which is to be measured, it is assured that the latter exposure will be within the linear range of response of the film if the measured densities resulting from the second exposure lie within the linear range of densities defined by the central steps in the image of the step-wedge.

Any type of radiation can be used to produce the images; the intensity of the final images produced should be congruent. In one embodiment, the step-wedge reference is prerecorded using a visible light source; measurements of interest may also be based on exposure from a radioactive source.

In order to preimage the step-wedge reference image on the film, a device is provided which includes a film holder with a masking system through which a limited region of the film can be exposed while the remainder of the film is optically isolated. Films are preimaged with visible light which has been parallelized. Collimation can be imposed by a lens system to modify the light source output.

In one embodiment of the method of quantitative analysis, specific nucleic acid sequences (DNA or RNA) to be quantified are identified by the attachment of a probe which has been previously made radioactive. Fragments from a chromosome of interest and fragments from a reference chromosome are simultaneously complexed with probes containing sequences specific to each, so that the relative amounts of the two can be determined. For example, a chromosome 21 fragment is spatially oriented relative to a fragment from another chromosome (e.g., chromosome 16). Both are labelled by hybridization, the former with a radioactive probe specific to chromosome 21 and the latter with a probe specific for the reference chromosome.

A film with the preimaged step-wedge is exposed to the radioactivity (e.g., radioactively labelled chromosome fragment-probe complexes) and developed; densitometric tracings are made.

If the heights of the peaks subsumed by the densitometric tracings of the two attachment sites lie within the linear range of response of the film as defined by the central steps in the image of the step-wedge, it can be assumed that the ratio of the areas is directly proportional to the relative amount of material present in each attachment site. If the peak heights do not lie within the defined linear range of absorption of the film, a re-exposure with another film can be done, with adjustment of the time of exposure as needed. Thus, the step-wedge image serves a purpose similar to that of a light meter in photography: it defines the appropriate exposure interval.

The method of the present invention can also be used by employing varying concentrations of the sample on the original gel, which supplies varying levels of response and serves the same purpose as variation in time of exposure. At least one of the given concentrations must produce peaks of absorbance that lie in the linear range of the film response curve.

Use of the method of the present invention makes it possible to reliably diagnose Down Syndrome both pre- and postnatally. It provides an accurate diagnosis for Down Syndrome samples that do not involve Trisomy 21 and have hitherto been difficult to assess. It has also been used to establish the genetic basis of Alzheimer's disease as an alteration in amount of the quantity of a specific subsection of chromosome 21, near to or within the location of the Down Syndrome DNA. Schweber, M. et al., *Neurology,* 37 (4), (1987). Thus, it can be used for direct, presymptomatic diagnosis of Alzheimer's disease. It can further be employed in prenatal and presymptomatic diagnosis of any genetic condition which has as its basis an alteration in the quantity of specific DNA sequences.

In a modification of the method, the film may be exposed in separate regions to the tagged molecules and to a standard gradient reference, such as a standard radioactive source with multiple levels of activity.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 4 shows densitometric tracings done on a Shimadzu Dual-Wavelength TLC Scanner of a silvered differential-density step-gradient with defined increments of absorbance.

In FIG. 9A, $A_1/A_2 = 1.36$; in FIG. 9B, $A_1/A_2 = 3.17$.

DETAILED DESCRIPTION OF THE INVENTION

The present invention relates to a method for accurate quantitation of components of a sample, such as DNA and RNA, which ensures that the signal deposited on film by components identified by attaching radioactively labelled probes lies within the linear area of response of the film. It can be modified for use with proteins. It also relates to a device useful in the preparation of film to be used in the method of the present invention.

Figure 2:
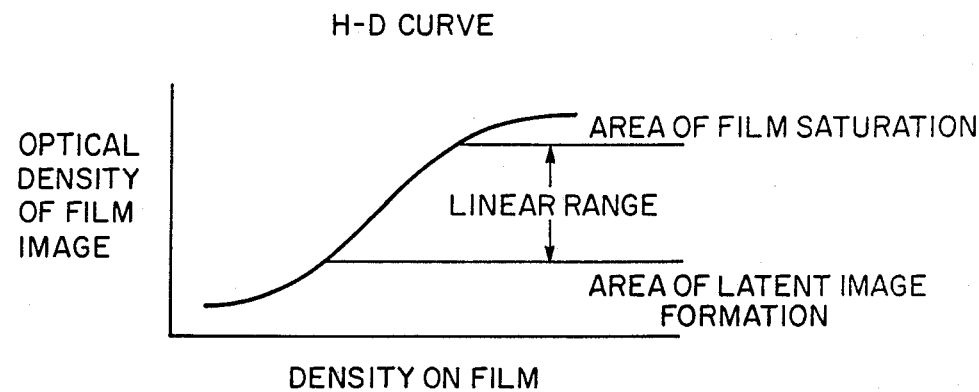
FIG. 2 is an illustration of a typical film response to exposure, the H-D curve.

Films, including X-ray film, contain only a limited region in which the film's response to a signal's intensity are linearly related. FIG. 2 represents a typical response of a film exposed to light; the resulting H-D curve shows that the linear area of the film's response curve is only a limited segment of the total response and is flanked by two regions (area of latent image formation and area of film saturation) in which the signal intensity and the film response are nonlinearly rlated.

To obtain accurate measurement of the amount of material generating a signal on film, the intensity of that signal must be controlled so that it lies within the central, linear area of response of the film. Laskey has described preflashing of film to bypass the stage called latent image formation. However, the optimal level of pre-exposure remains unclear. For example, Laskey specifies an absorbance increase of 0.15 Å 540 and Southern prefers 0.05 Å600. Laskey, R. and A. Mills, *European Journal of Biochemistry*, 56: 335–341 (1975); Southern, E., *In: Methods in Enzymology*, 60: 152–175, Academic Press (1979). The problem of overexposure of signal (i.e., the upper end of the curve) has to the present remained unsolved. Lack of control of the intensity of the image formed makes quantitative measurement unreliable. Pooling of multiple repeats (multiple measurements) has been used in an attempt to obviate this problem, but the variability of uncontrolled results cannot be expected to be random. In the method of the present invention, the use of an internal control system (i.e., internal calibration) resolves this problem.

Although recombinant DNA technology offers great promise for analytical and diagnostic applications, such methods have not to the present time been useful for conditions involving quantitative alterations because of the variability in the techniques used. Much effort has been focused on resolving this problem, with little success. Through the use of the method and apparatus of the present invention, however, it is now possible to assure that densitometric analysis of assays are linearly (directly) related to the amount of DNA or RNA present in a sample and, thus, to accurately determine that amount.

Figure 4B:
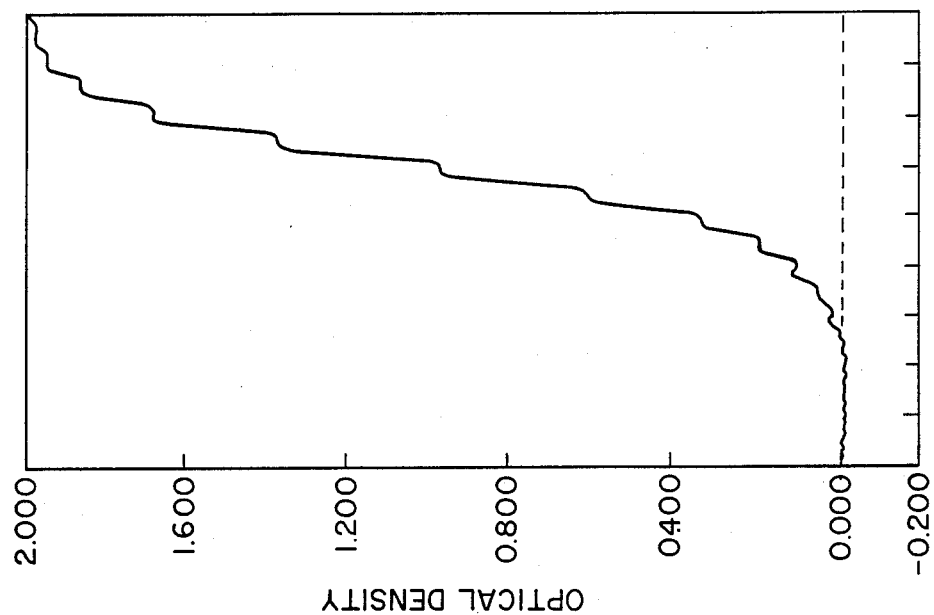
FIG. 4B shows the densitometric tracing of the film image of the same silvered step-wedge gradient, showing that only a few central levels of absorbancy define the linear range of response of the film.
Figure 4A:
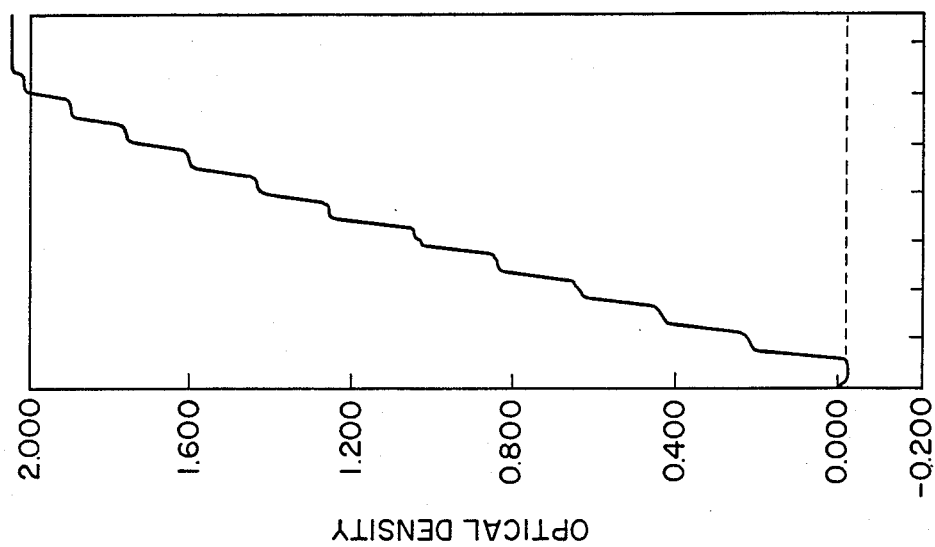
FIG. 4A shows a direct tracing of the step-wedge (reference) directly, distinguishing 12 incremented density steps.

In the method of the present invention, a silvered differential-density step-wedge gradient with defined increments of absorbance bracketing 0 to 100% absorption is preimaged on the film. The importance of control of the intensity of the film image is illustrated in FIG. 4. Direct densitometric tracing of the step-wedge permits detection of the complete density range, as shown in FIG. 4A. It defines 12 steps of equivalent density increment. Tracing of the image of the step-wedge registered on the film, however, shows that only a limited number of central levels of absorbancy lie within the sensitive range of the film response, as shown in FIG. 4B. Other images on the film will be linearly related to the amount of material generating their presence only if the magnitude of their signal lies within the density of the controlled central steps.

Preimaging of the step-wedge provides a gauge for the Southern blot exposure. That is, if bands are produced on the film which have densities within the linear range of film response, areas subsumed by densitometric tracings of the bands will reflect the amount of material to which the probes attach. If the magnitude of the band's signal does lie within that density region, accurate determination of quantitative relationships, directly from area measurements traced, is assured. Results can be obtained from tracings of single gel lanes; no pooling of results or statistical adjustment is necessary. Therefore, it is possible to use the present method for quantifying DNA in an individual sample and for diagnosing conditions whose bases lie in abnormal quantities of DNA in cells. It can be used, for example, for diagnosing Down Syndrome and for diagnosing Alzheimer's Disease.

The present invention specifically relates to a method which makes it possible to adjust the exposure time of Southern blots labelled by radioactive probes and, as a result, to insure accurate quantification of a biological molecule (e.g., DNA or RNA of interest) which is identified through hybridization by radioactively-labelled probes. As explained above, the response of a film to a signal is S-shaped and only a portion of the film response is linearly related to the signal received. If the signal generated or produced by the material of interest (e.g., DNA, RNA) falls within the linear portion of the film response, the material can be accurately quantified.

According to the method of the present invention, it is assured that the signal generated by the material of interest falls within the linear portion by introducing an image of a silvered step-wedge on the film. This is done by preimaging a step-wedge gradient on a restricted portion of the film with visible light, prior to its exposure to the Southern blots. Densitometric tracings are then done of both the step-wedge image produced by visible light and the band images produced by radioactivity from the probe attachments. If the heights of the tracings of the band images produced by radioactivity from the probes lie within the linear range of film response as defined by tracings of the step-wedge image, it is assured that the film response of the bands is linearly related to the amount of material on the gel identified by probe attachments.

The areas subsumed by the bands will accurately and directly reflect the amount of labelled material present at each location. An important advantage of the method of the present invention is that internal controls are incorporated and make internal calibration possible. As a result, comparative ratios of quantities of materials (e.g., sample DNA being quantified and reference DNA) are determined.

The method of the present invention can be used to accurately quantify any DNA, RNA or other biological molecule of interest in a sample. It has been shown to be a sensitive and accurate method for determining DNA ratios in blood, brains, and cultured cells. That is, it has been shown to be sensitive and accurate for determining the quantity of DNA of interest in single samples and for detecting a difference between the quantity of DNA of interest and the quantity of reference DNA present in a sample.

Figure 3:
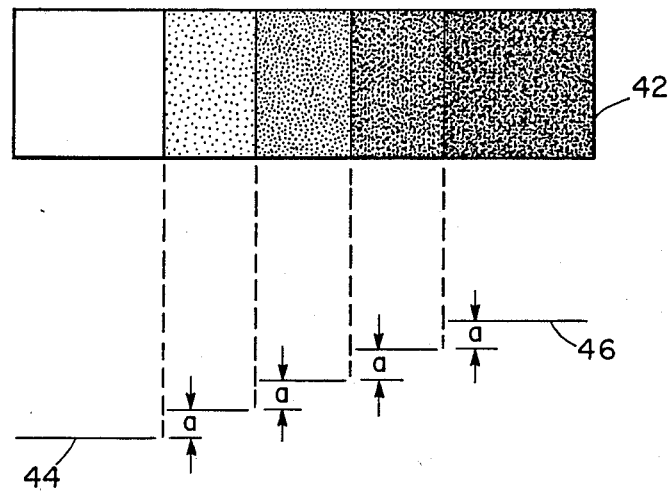
FIG. 3 is an illustration of a reference step-wedge gradient image applied to a film in accordance with the present invention.

The present invention thus provides assurance that all film samples on which a scientist or diagnostician relies are exposed in the linear response region of the film frame. To that end, the film is pre-exposed in a limited region thereof with a standard reference 42, such as that illustrated in the upper section of FIG. 3. Although only five regions of different densities are shown, additional regions may be provided; in general, 12 such regions are used. When the film is exposed to provide the reference image, a densitometer tracing of the reference is made, as shown at the bottom of FIG. 3. The tracing ranges from a level of minimum exposure at 46 exposure at 44 to a level of maximum exposure at 46 through steps equally incremented at density difference "a".

Figure 5:
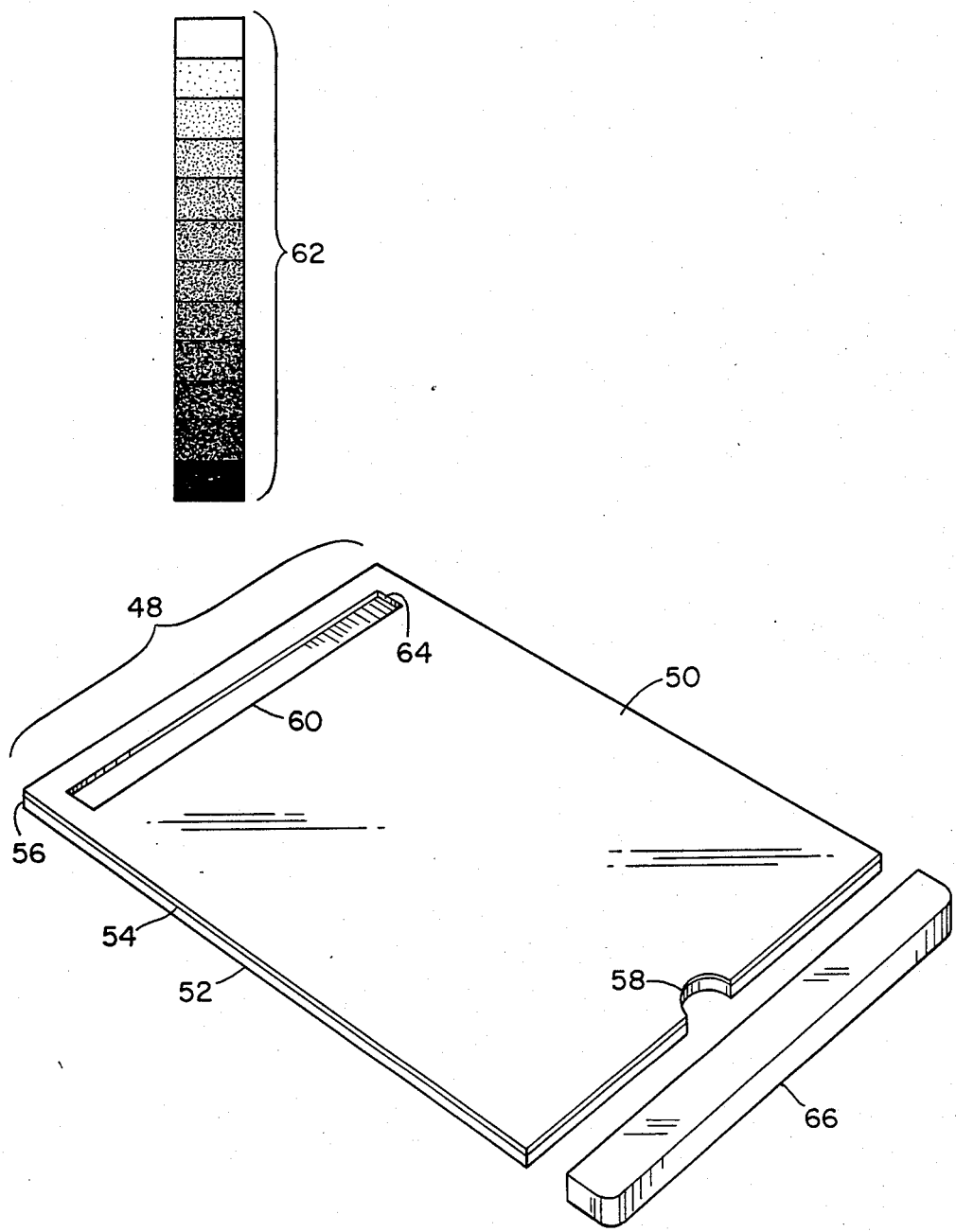
FIG. 5 is a plan view of apparatus for imaging a density gradient reference onto a film.

The density reference can be formed on the film using the device of FIG. 5. As shown in FIG. 5, a plate assembly 48 is used to hold the film to ensure that specified film regions can be exposed successively. The plate assembly 48 has an upper plate 50, a lower plate 52, two side walls 54 (one not shown) and one end wall 56. The two plates are separated from each other by a narrow space (e.g., sufficiently wide to allow the X-ray film to be inserted). Plates 50 and 52 have a semicircular cut 58 at one end for ease in removing the film. Upper plate 50 has an opening 60 cut in it close to the end opposite the circular cut 58; opening 60 serves as a window through which the X-ray film, once inserted between upper plate 50 and lower plate 52, can be exposed in a carefully-defined area to a light source. At opening 60, a step-wedge gradient 62 is positioned in such a manner that when the underlying X-ray film is exposed to light through the step-wedge, an internal calibration standard is imaged on the film in the area defined by the opening. Opening 60 has a lip on each end 64, onto which the step-wedge gradient 62 is placed, with the result that the step-wedge gradient is in close proximity to the underlying film. The end having the semi-circular cut 58 is open to make it possible to insert and remove the X-ray film between upper plate 50 and lower plate 52. After the X-ray film has been inserted, cap 66 is placed over the open end, thus the sealing plate assembly and preventing the X-ray film from being exposed to light (other than at window 60).

Although the film in many applications will be subsequently exposed with radiation from radioactive material, it is particularly convenient to expose the density reference with a visible light source. The light source used for this purpose can be from any range of the light spectrum to which the film is sensitive (e.g., X-ray, visible light, electrons); any light source which allows this can be used.

There is a difference between light and radioactive sensitivization of film emulsions because of the difference in the quantum energy levels of the two types of radiation. Visible light requires 5 to 7 photons to produce a signal on the film and thus exhibits a large first stage lag on the film response. The higher energy of the radioactive decay products produces a reaction from only a single photon, which results in negligible latent image formation. The adjustment in signal to coordinate the two types of sources on the same piece of film is described below. This difference in type of energy generating the signal does not affect quantification; that is, the same form of radiation used to obtain the experimental results need not be used to produce the densitometer reference image. The important consideration is that the radioactive signal be adjusted so that its maximum lies within the linear range of the film, which is defined by the step-wedge image. Essentially the step-wedge image on the film acts as a radiation meter, allowing determination of the appropriateness of the time of exposure (with repeated exposure with adjusted time where necessary). Step-wedges which can be used in carrying out the method of the present invention are available from the Eastman Kodak Company. For example, a photographic neutral density attenuator or photographic step tablet such as a No. 2 calibrated neutral density attenuator which has a density range of 0.05–3.05, a density increment of 0.15 and a step width of 5 mm (Catalog No. 152 3406, 1982 Eastman Kodak Neutral Density Attenuators Catalog, pp. 12 and 15) can be used in the method and device of the present invention.

Figure 6:
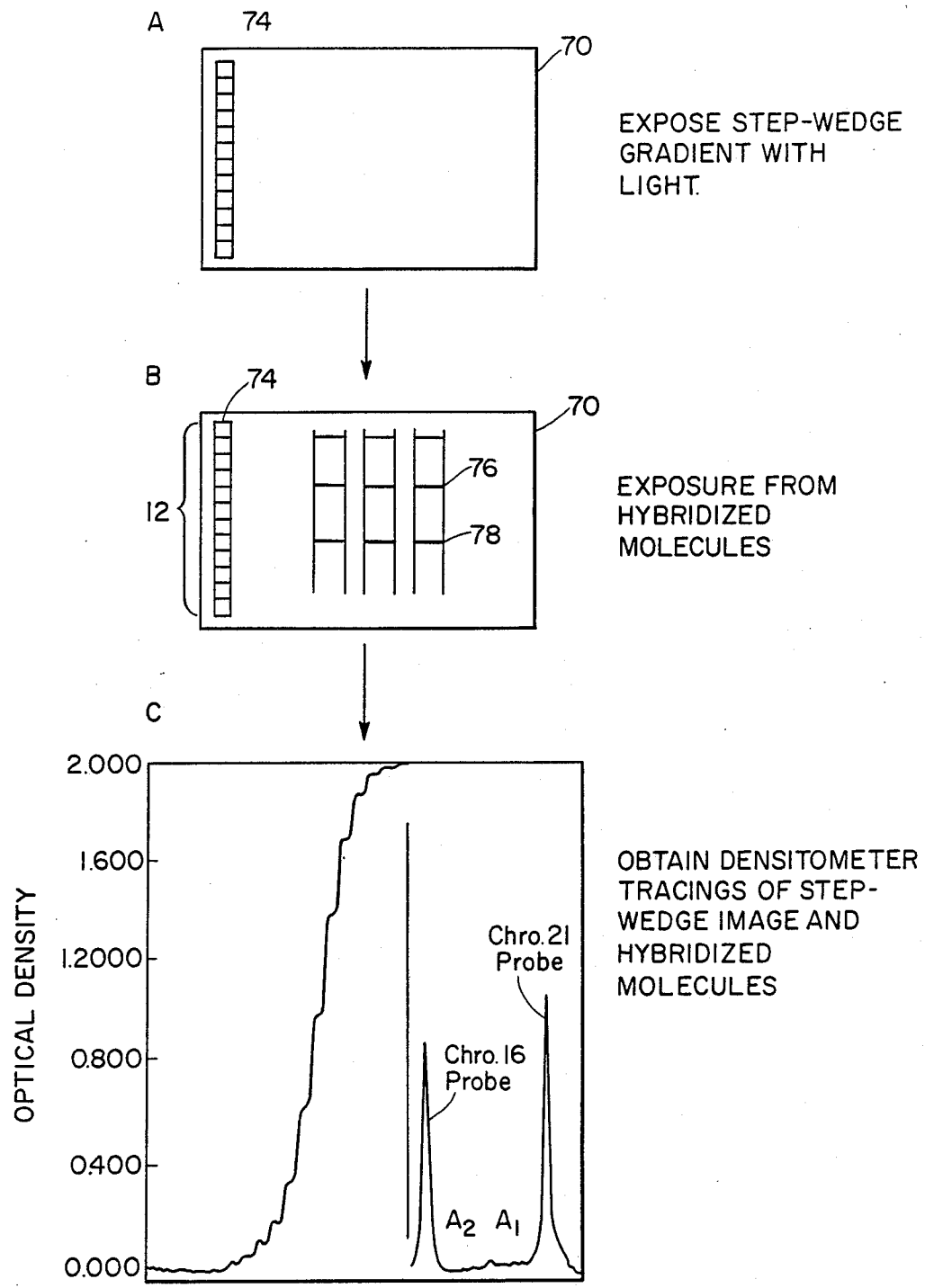
FIG. 6 is an illustration of a method of handling film in accordance with this invention to diagnose Down Syndrome using the method of FIG. 1.

Once the densitometer reference has been imaged onto the small region of the film using the device of FIG. 5 illustrated as step A in FIG. 6, film 70 is removed from the device and can be used in experimentation. Thus, in the experimental method of FIG. 1, the film having the gradient pre-exposed thereon is utilized in step F and is exposed to the hybridized molecules on the blot. Several successive exposures of several sheets of film may be needed in order to assure that one of the exposures will provide densitometer tracings within the linear range of the film. Further, as in the method to be described below for diagnosis of Down Syndrome, two bands of radioactive signals 76 and 78 may be formed on the film in each lane of exposure, to provide a reference signal. When the film is subsequently developed and densitometer tracings are made, the density reference image provides a tracing like that shown at the left of FIG. 6C; if the density reference image includes the linear response range of the film, central steps of equal size can be seen in the central part of the tracing as shown. A tracing of the bands 76 and 78 should provide density tracings whose peaks lie within the central steps of the tracing of reference 74. If not, that film is discarded and another applied, with appropriate adjustment of exposure.

The method and device described above with reference to the figures are useful in quantifying DNA and RNA. They are directly useful in the diagnosis or identification of genetic disorders whose basis is a quantitative change in DNA or RNA. As described below and in the Examples which follow, they make it possible to diagnose disorders, such as Down Syndrome and Alzheimer's Disease, which have been shown to have as their basis an alteration in the amount of DNA present in cells. Both Down Syndrome and Alzheimer's Disease involve increases in certain DNA's present in cells of affected individuals. The method can also be used to diagnose conditions in which the quantitative change is a decrease in the amount of specific DNA in cells.

It has been shown that reliable quantitative data can be obtained using the system of the present invention. For this purpose, a tissue culture facility was established and cells grown from monosomy, disomy, and trisomy chromosome 21 fibroblast cell lines. This work is described in detail in Example 1.

Ideal ratios between chromosome 21 and control chromosome probes in the fibroblast cell lines are $\frac{1}{2}$, 2/2, and 3/2, respectively. The parameters measured by densitometry are $A_1$ and $A_2$, the areas subsumed by tracings of film signals generated by the hybridized clones. The results of the $A_1/A_2$ determinations obtained were expected to be affected by a large number of factors. Mathematically the situation can be minimally expressed for each radioactively labelled band on the Southern blots as:

$$A_x=(\alpha p_x)(\beta s_x)(\gamma m_x)(\epsilon t_x)(\zeta r_x)(\eta c_x)(\theta D_x)$$

where A=area, p=probe size, s=specific activity, m=degree of mismatch, t=differential temperature response due to sequence heterogeneity, r=degree of linear response of the radioactivity decay curve, c=compaction, and D=the amount of chromosome DNA. The Greek symbols are all constants.

Thus, for comparative ratios $A_1/A_2=f\{D_1/D_2\}$.

It is the ideal ratio of $D_1/D_2$ that exists in the cell, but ratios measured are those of $A_1/A_2$. Some of the affecting factors (such as p and s) can be determined; others (m and t) cannot. None of the constants are known; thus, the cumulative effect on the measurement could not be anticipated. Experimentally it was found that the various factors do not interfere with discriminatory capability. However, they do affect the numerical value of the ratios. Thus, the results obtained are evaluated not for their precise numerical value, but for their comparative worth.

The results of this work are presented in the Examples presented below. The following is a description of the general approach and techniques used, which can be applied to quantification of any DNA or RNA of interest through use of the method of the present invention.

According to the method of the present invention, a carefully-defined section of X-ray film is exposed, using a device such as that shown in FIG. 5, to visible light (or any type of radiation) which passes through a silvered differential-density step gradient which has defined increments of absorbance. As a result, the step gradient or step-wedge is imaged onto the film in the limited exposed area, leaving the remainder of the film unexposed. Densitometric tracing of the resulting film image produces an S-shaped curve, as shown in FIG. 4B, with only a few steps having absorbancies which fall within the linear range of the film response. Direct measure of the quantity of material which is identified by radiation is possible if the images of it are controlled so that they occur with densities in the linear area regions. The linear range of response can be made to occur in the central area of the absorbancy scale by adjusting exposure of the step-wedge.

The undeveloped X-ray film, preimaged with the step-wedge reference image, is then exposed to the labelled sample to be analyzed. This is done, for example, by applying the film to radioactively-labelled Southern blots, thus exposing the film to the radioactivity. The Southern blots can include, for example, DNA of interest (e.g., DNA to be quantified) labelled by hybridization with a radioactive probe containing sequences specific for the DNA from the chromosome of interest and reference DNA from another chromosome, each labelled by hybridization with a (different) specific radioactive probe. The DNA of interest can be a 21q22 fragment and the reference DNA can be chromosome 16 DNA.

The film is subsequently developed and a densitometric tracing is done along the step-wedge image and along each lane resulting from exposure to the Southern blot. If the peaks on the tracing from the lanes are not in the linear area of response of the X-ray film, another exposure to the blot is carried out. If the peaks on the tracing lie within the linear area, the ratio of the areas under the densitometric tracings of the peaks is directly related to the quantity of each type of DNA present on the gel and the quantity can be accurately determined.

The practical problems of quantitation with recombinant DNA methods such as described here are formidable. For example, to quantify Southern blots, linearity of response should be maintained throughout all procedures. DNA should be isolated from cells being analyzed in such a manner that proportionalities (i.e., relative amounts of each molecular species of DNA) present in the nucleus are maintained. It should also be digested, dispersed on a gel and transferred to a support stoichiometrically. Essentially quantitative recoveries can be maintained throughout, although loss of small fragments may occur. Laskey, R., *Methods in Enzymology*, 65: 363-375 (1978). One of the major obstacles has been the necessity of maintaining linearity of response throughout the stages of the procedure; this has been overcome in the development of the method of the present invention. The stages are described below.

The first stage of preparation involves the isolation of DNA, its digestion with restriction site endonucleases, and dispersal on a gel. It has previously been established that quantitative recoveries are maintained throughout these procedures. Laskey, R., *Methods in Enzymology*, 65: 363-375 (1978).

In the next stages, the DNA fragments on the gel should be transferred to support systems stoichiometrically and with no loss of small fragments. Such recoveries are possible with the use of DBM paper, which covalently binds to DNA and allows for quantitative recovery of even very small fragments when it is coupled to an electro-transfer system. The specific DNA fragment (the DNA fragment of interest—e.g., a 21q22 fragment) on the support system is identified or localized by the attachment of a specific probe which a homologous sequence to the DNA fragment of interest. The probe has been labelled to a high level of intensity by nick-translation or end-labelling, using known techniques such as those described by Maniatis, T. et al., *Molecular Cloning: A laboratory Approach*, Cold Spring Harbor Laboratory Press (1982), the teachings of which are incorporated herein by reference. Such fragments or molecules, which have a radioactively-labelled probe attached, are referred to herein as radioactively-identified fragments or molecules. Attachment (hybridization) of the probe strands to a DNA fragment having complementary strands occurs molecularly and, as a result, the amount of probe which can attach reflects the quantity of DNA of interest available for attachment through hybridization.

The technical problems are most acute in the next stages, in which photographic film exposures of the radioactivity contained in the probe must be made measureable. There is criticality of control if the amount of a nucleic acid sequence of interest present in a gel is to be accurately quantified by measurement of the tracks produced in an emulsion by a radioactively-labelled probe attached to that nucleic acid sequence. The amount of radioactivity allowed to pass into the emulsion must be carefully controlled (i.e., neither too little nor too much exposure can occur). Underexposure will produce separated tracks which cannot be reliably traced; overexposure will saturate the emulsion and produce inaccurate readings. The control of the exposure of the film must be confined to the linear range of response of the film.

The last stage of the procedure requires microdensitometric tracing of the exposed film and measurement of the areas subsumed, e.g., by planimetric devices or automated computerized densitometric devices. Measurement of differing amounts of various chromosomal materials in humans using this technique has been reported; McDermid, H. et al., *Science*, 232: 646–648 (1986); Wolf, S. et al., *Cell*, 21: 95–102 (1980), including measurements on chromosome 21; Junien, C. et al., *American Journal of Human Genetics*, 35: 584–591 (1983); Davies, K. et al., *Genetics*, 66 (1984); Devine, E. et al., *Annals of the New York Academy of Sciences*, 450: 69–83 (1985). None have been controlled and, hence, were not reproducible or reliable. A recent attempt at exposure control has used a dot blot series of radioactive signal increments as a control gauge; pooling of repeated measurements was still required. Delabar, J.-M. et al., *Science*, 235: 1390–1394 (1987).

By using internally-controlled, relative ratios, with controlled exposure, the method described herein obviates many of the critical difficulties involved in standardizations. These procedures can be used to measure the amount of chromosome 21 in human cells from a single sample, thus providing a method, for example, of diagnosing Down Syndrome.

Diagnosis of Down Syndrome

The single most common chromosomal abnormality in humans is Down Syndrome, which is estimated as being responsible for 14 of the 56 chromosomal abnormalities known to occur per 10,000 live births in the U.S. The health care burden from Down Syndrome is indicated by estimates that individuals with this single condition constitute 25–30% of the severely mentally retarded population. Pueschel, S. and J. Rynders (ed.), *Down Syndrome: New Perspectives in Biomedicine and the Behavioral Sciences*, Garland Publishers (1981).

Despite the identification in 1959 of Trisomy 21 as the causative factor in Down Syndrome, there has been little progress toward an understanding of the mechanism of its basic etiology.

Prenatal diagnostic procedures for Down Syndrome have to date been limited to direct karyotypic analysis, with amniocentesis involving a number of disadvantages, as described above.

Because Down Syndrome is a genetic condition, involving only molecular changes in DNA amount, diagnosis at the molecular genetic level should be possible. However, this cannot be done with presently available techniques. Experimental results at the level of gene products using cultured cells have been disappointing; only a slight statistical difference has been found when RNA in cells from normal and affected individuals have been compared and no differences have been observed at the polypeptide level.

Because Down Syndrome involves a quantitative change in genomic DNA, a more direct approach has been developed, which is targeted directly at the primary DNA level by the use of recombinant DNA (RDNA) technology, and is described below. Use of the method of quantifying DNA, as described above, makes it possible to accurately and reliably detect abnormal (e.g., in the case of Down Syndrome, increased) levels of DNA from chromosome 21 in biological samples and, thus, to diagnose Down Syndrome.

The advantages of the new method are multiple. Such tests performed on cells obtained by amniocentesis can be completed in 2 to 3 days (instead of 3 to 4 weeks as required by present methods); the cost should be substantially lower than with current methods. In addition, there will no longer be a reliance on amniocentesis. It has been shown that sufficient DNA for a Southern blot type analysis can be obtained by trophoblastic excision of a single chorionic vilus as early as the fourth week of pregnancy. Williamson, R. et al., *Lancet, ii*: 1125–1127 (1981). Thus, a much earlier detection system is available.

A further development, which would be much less invasive, is the possibility of using a maternal blood sample as the source of material. Fetal cells are known to circulate in maternal blood and enrichment of that fetal cell population to the 10% level is possible by use of a fluorescent-activated cell sorter system. Herzenberg, L. et al., *Proceedings of National Academy of Sciences*, U.S.A. 76: 1453–1455, (1979); Medearis, A. et al., *American Journal of Obstetrics and Gynecology*, 148: 290–295, (1984). In principle, the delicacy of discrimination possible by a quantitative radioactive reaction should permit the eventual detection of a triploid amount of a portion of chromosome 21 in even 10% of the cells by suitable manipulation of the sensitivity of the system, including switching to a cosmid vector. Use of this system should be possible as a safe, simple, relatively inexpensive, early, non-invasive prenatal diagnostic system which makes use of a maternal blood sample. The development of similar, simpler, faster, safer and earlier detection systems for other diseases as well will permit more widespread prenatal testing for genetic conditions involving quantitative nucleic acid changes.

As described above, Down Syndrome is caused by a change in the relative amount of DNA. Generally, Down Syndrome is caused by Trisomy 21, with three complete chromosome copies present in cells due to nondisjunction; two copies of chromosome 21 are present in normal cells. Other genomic mechanisms which result in only partial triplication of chromosome 21 also generate the syndrome. Patterson, D. and V. Schandle, *Banbury Report*, 15: 215–223 (1983); Thuline, H. C., *In: New Perspectives on Down Syndrome*, Pueschel, S. M. et al., (ed.) Brookes Publishing, pp. 24–39 (1986). Because all known forms of Down Syndrome involve triplication of a specific region of chromosome 21, direct measurement has been sought by application of recombinant techniques. However, application for diagnostic purposes has not been possible previously because of methodological difficulties.

Figure 1:
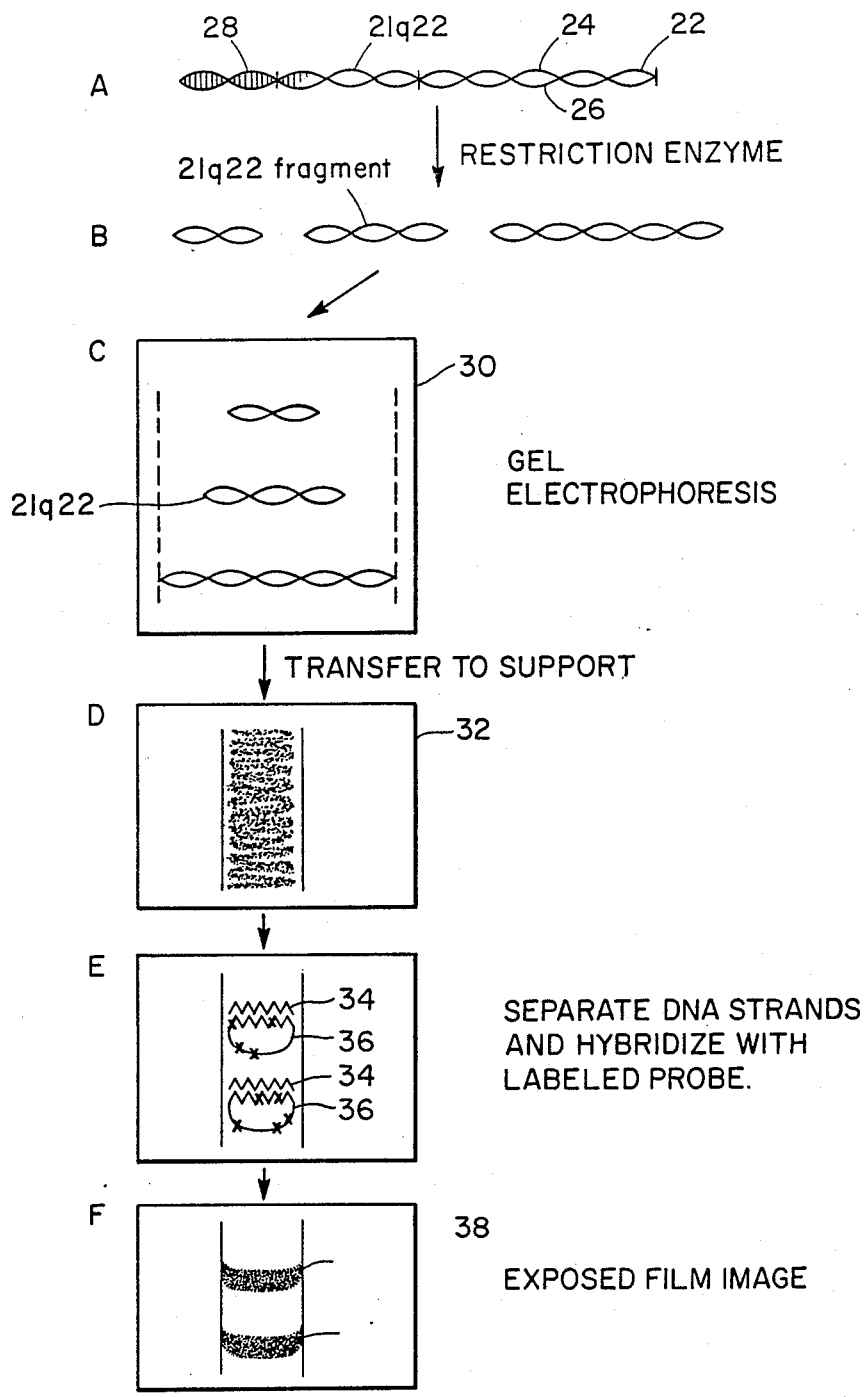
FIG. 1 is an illustration of a prior art method of quantitative analysis which makes use of DNA probes.

The method of FIG. 1 modified by the density reference method of FIG. 6 can be used to determine the relative quantity of specific chromosome 21 DNA. The amount of this relative to the amount of another (reference) chromosome, (e.g., chromosome 16) from the same individual is determined; in this case, chromosome 16 serves as an internal reference. That is, through its use, it is possible to calculate an internally-controlled, relative ratio and determine whether the individual has an excess of chromosome 21 amount. A 3/2 ratio of these two chromosomes (21/16) is expected from a Down Syndrome sample; a 2/2 ratio is found in unaffected individuals.

The following method can be used to diagnose Down Syndrome: DNA is isolated from a biological sample and digested with restriction enzymes. Among others, PST, Hin dIII, Hin cII, Bgl I, Sal, and Eco RI restriction enzymes are used. Using electrophoresis, the fragmented DNA is then spatially-oriented in a gel, based on fragment size. The spatially oriented DNA fragments are transferred to an appropriate support, such as Zeta TM probe support, which is suitable for carrying the DNA fragments during subsequent processing. The DNA strands are separated by altering the pH of buffer in which the support is immersed. Thereafter, two radioactively-labelled plasmid probes which have sequences homologous, respectively, to chromosome 21 and to chromosome 16 are hybridized with the fragments of separated DNA strands on the support, under conditions appropriate for reannealing of complementary nucleic acid strands to occur. The number of plasmids which attach to chromosome 21 and to the 16 fragments with homologous sequences on the support is directly related to the number of DNA molecules from each chromosome on the support.

With the radioactive plasmids thus attached, the film is exposed to the radioactive signal in the dark at $-80°$ C. An initial exposure of limited duration is made to test conditions. Subsequent exposures are made as needed to appropriately adjust the signals, using separate film sheets that have been pre-imprinted with the step-wedge density image. The radioactively identified genomic DNA fragments on the support produce dark bands 76 and 78 on the film (FIG. 6). The degree of the intensity of the images produced is a function of the respective quantities of chromosome 16 and of Down Syndrome DNA on chromosome 21. A densitometer tracing of both the step-wedge reference image and the two bands from radioactive exposure provides the output of FIG. 6C. If the resulting densities of the two bands are within the linear response region of the film (as indicated by the tracing of the step-wedge image), the comparative ratio of the areas under the peaks produced by bands 76 and 78 quantifies the relative amounts of chromosome 16 and of chromosome band 21 material.

The use of the reference chromosome 16 in the above example allows for comparative quantification of the relative amount of chromosome 21 material present. Another way to quantify chromosomal DNA in a sample is to expose the experimental radioactive support with a density reference having known levels of radioactivity thereon. Several different levels of known radioactivity may be provided along a strip to provide a density gradient, as shown at the left of FIG. 6C.

An alternative reference system may be used alone or in conjunction with the densitometric reference system previously described. For example, radioactive molecules deposited to form equal incremented amounts of radioactivity can provide an equally incremented step output defining the linear response range of the film. Even where the radioactive sources are not equally incremented, they will provide a predetermined relative determination to define the linear response range of the film, when measured by a radioactive sensitive detector. A radioactive reference system can be exposed with the experimentally-produced radioactive bands and can serve the function of the previously described density reference system.

Diagnosis of Alzheimer's Disease

The method of quantification of cellular DNA of the present invention can also be used to diagnose Alzheimer's Disease (AD). The following is a description of the genetic basis of Alzheimer's Disease and of use of the method of the present invention in its diagnosis.

Alzheimer's Disease is expressed in a threefold nosology: anatomical, biochemical and behavioral. Previous work has shown similarities and interrelations between Alzheimer's Disease and Down Syndrome. *Alzheimer's Disease, Down's Syndrome, and Aging*, Sinex, F. and Merril, C., ed., Annals of the New York Academy of Sciences, 296(1982).

This led to exploration of the possibility that there is also a similarity in the etiology of the two. It is well known that Down Syndrome involves a quantitative change in a specific DNA segment on band 21q22 of chromosome 21. The idea was advanced that changes at the molecular level in the amount of specific DNA on chromosome 21 are involved in the etiology of Alzheimer's Disease. Schweber, M., *Annals of the New York Academy of Science*, 450: 223–238 (1985). Specifically, the hypothesis tested was that Alzheimer's Disease is caused by triplication of a small amount of DNA on chromosome 21 near to or within the location of Down Syndrome DNA. This work is described in detail in Example II.

Unlike Down Syndrome, in which genetic alteration usually occurs at such a gross level that microscopic detection is possible, no characteristic karyotypic changes have been found for Alzheimer's Disease. Measurements of the DNA level by flow cytometry to detect aneuploidy has also shown no gross alterations. Cook-Deegan, E. and J. Austin, *American Journal of Medical Genetics*, 15: 511–513 (1983). However, minute quantative changes in genetic makeup at the molecular level cannot be detected with these methods.

This work has been extended to assess the ability of the method described above to detect alterations in the DNA content of various tissues from Alzheimer's Disease patients. This is described in Example II.

As a result of the work described herein, it is now possible to quantify reliably and accurately DNA, RNA, or other materials (e.g., proteins, polypeptides) at a level previously not possible because of the lack of a method capable of quantitating results produced by recombinant DNA techniques.

Although the work is described herein with specific reference to detection of alterations in genetic material associated with Down Syndrome and Alzheimer's Disease, the method can be extended to other conditions and diseases associated with alterations at the molecular level. That is, it can be extended to other situations in which quantification of chromosomal DNA (or RNA, proteins) is needed. It is particularly valuable because it makes possible the accurate measurement of DNA of interest in an individual sample, with no pooling or statistical manipulation necessary.

For example, it can be extended to other genetic conditions and diseases whose molecular basis is understood. The second most common genetic abnormality affecting newborns (Down Syndrome is first) involves quantitative changes in the amount of sex chromosome material. Establishment of a simple, fast, and reliable test for quantitative variations for the amount of specific DNA on chromosome 21 present in a fetal cells can easily be extended to measure the quantity of X and Y chromosomal material present by simply using different probes. For example, the method of the present invention could be used to diagnose Turner's Syndrome (XO) and Klinefelter's Syndrome (XXY) through the use of cloned human X and Y DNA fragments. A range of tests for quantitative variation in the genome are thus practicable. It is reasonable to expect that such tests will become possible using only a maternal blood sample as the source of DNA.

A further possible application of the use of quantitative measurement is the examination of genetic conditions for which the molecular basis of the abnormalities has not been established. This approach would afford a new way of examining a multitude of genetic diseases about which little is presently known. The establishment of the molecular basis of the haemoglobinopathies has been a remarkable accomplishment, but one which has taken over 20 years and the efforts of a multitude of researchers and vast resources. The majority of genetic diseases affect relatively few individuals. As a result, it is difficult to imagine that comparable levels of activity will be expended on all of them. Although it is not clear how many of the uncharacterized genetic diseases involve quantitative changes in the genome, it seems likely that at least some of them do. These diseases could be detected by a wide-spectrum, quantititative screening test based on the method of the present invention.

While the invention has been particularly shown and described with reference to a preferred embodiment thereof, it will be understood by those skilled in the art that various changes in form and details may be made therein without departing from the spirit and scope of the invention as defined by the appended claims.

The device of FIG. 5 for preexposing the film through the silvered step-wedge gradient may be significantly modified as appropriate or needed for a given application. For example, the film might be clamped between two hinged plates which permit exposure of the film only through the silvered gradient mask. A significant aspect of the device in any form is that it prevents exposure of a substantial region of the film while providing a densitometer reference on a limited region.

Although the invention has been specifically described with respect to diagnosis of Down Syndrome and Alzheimer's Disease, it can also be applied to a wide range of quantitative analyses, as described above. Its use permits diagnosis of any genetic condition which involves a quantitative change in genomic DNA.

Further, although the description has used the detection of DNA as an example, the method is also applicable to other biological materials. These materials include, in addition to DNA, RNA and proteins (including fragments thereof, such as oligonucleotides, peptides). For example, variation in the quantity of celluar RNA may occur in a variety of disease states and as a result of normal processes of growth and development. Further usage of the system with proteins or fragments thereof is also possible. The term biological molecule is used herein to refer to DNA, RNA, proteins, and fragments or segments thereof. Also, certain aspects of the method can be extended to analyses which do not rely on radioactive probes but which rely on another source of exposure for providing densitometer tracings.

EXAMPLE I

Discrimination Among Varying Amounts of Chromosome 21

Tests were carried out on DNA isolated from fibroblast monosomy, disomy, and trisomy chromosome 21 cell lines to ascertain whether discriminatory capability was possible. Ideal ratios between chromosome 21 and reference chromosomes ($D_1/D_2$) for these lines are $\frac{1}{2}$, 2/2, and 3/2. The parameters measured by densitometry are $A_1$ and $A_2$, the areas subsumed by tracings of film signals generated by the hybridized clones. With controlled exposure, the ratio $A_1/A_2$ is a direct function of $D_1/D_2$. The numerical values of $A_1/A_2$ are expected to vary between blots; within one blot, however, comparisons of $A_1/A_2$ ratios of normal and affected tissues are informative.

DNA was isolated from the samples and digested using restriction enzymes (e.g., Hin dIII, PST, Eco RI), according to standard methods. Southern blots were made of the isolated genomic DNA. Maniatis, T. et. al., *Molecular Cloning: A Laboratory Manual*, Cold Spring Harbor Laboratory Press (1982). Cells were washed several times in Triton X, sucrose, Tris, magnesium buffer; o/n lysing was done with SDS and proteinase K; deproteinized with chloroform/isoamyl alcohol/phenol followed and DNA was precipitated in ethanol with sodium acetate. Digested DNA was run on a 1% agarose gel in a vertical rig (Blair craft Industries), and transferred manually o/n to nitrocellulose. Nick translation kits (BRL) were used to label the probes with 2 or more $^{32}P$ dxTP's (New England Nuclear). Prehybridization, hybridization, and washing followed standard protocols. Maniatis, T. et. al., *Molecular Cloning: A Laboratory Manual*, Cold Spring Harbor Laboratory Press (1982).

Under conditions appropriate for hybridization of complementary nucleic acid sequences, the transferred DNA was probed with radioactively labelled human cloned chromosome 21 fragments, including a fragment that localized to the Down's Syndrome site on chromosome 21. For this purpose, the fragment used was a unique sequence which localized at one end of the superoxide dismutase I (SOD) locus. The unique sequence used as a probe was a small subclone (4.2 Kb) near the 3' terminal of the SOD gene encompassing the fifth exon, with a unique sequence not present on any of the four pseudogenes for SOD which have been shown to be present on four chromosomes other than chromosome 21. Levanon, D. et al., *EMBO Journal*, 4: 77-84 (1985). For reference chromosome probing, a subclone from a different chromosome (a subclone of the ε-globin gene sequence of chromosome 16) was used. Baralle, F. et al., *Cell*, 221: 621-626 (1980). Both fragments were inserted into pBR 322. Each probe was tested separately to identify enzymes that produced nonoverlapping results. The hybrid formations produced by hybridization of sample DNA and labelled probe were assessed using the densitometric method described above. Using the cultured fibroblasts, controlled exposure according to the method described above permitted identification of the three chromosomal types as shown in Table 1.

Figure 7:
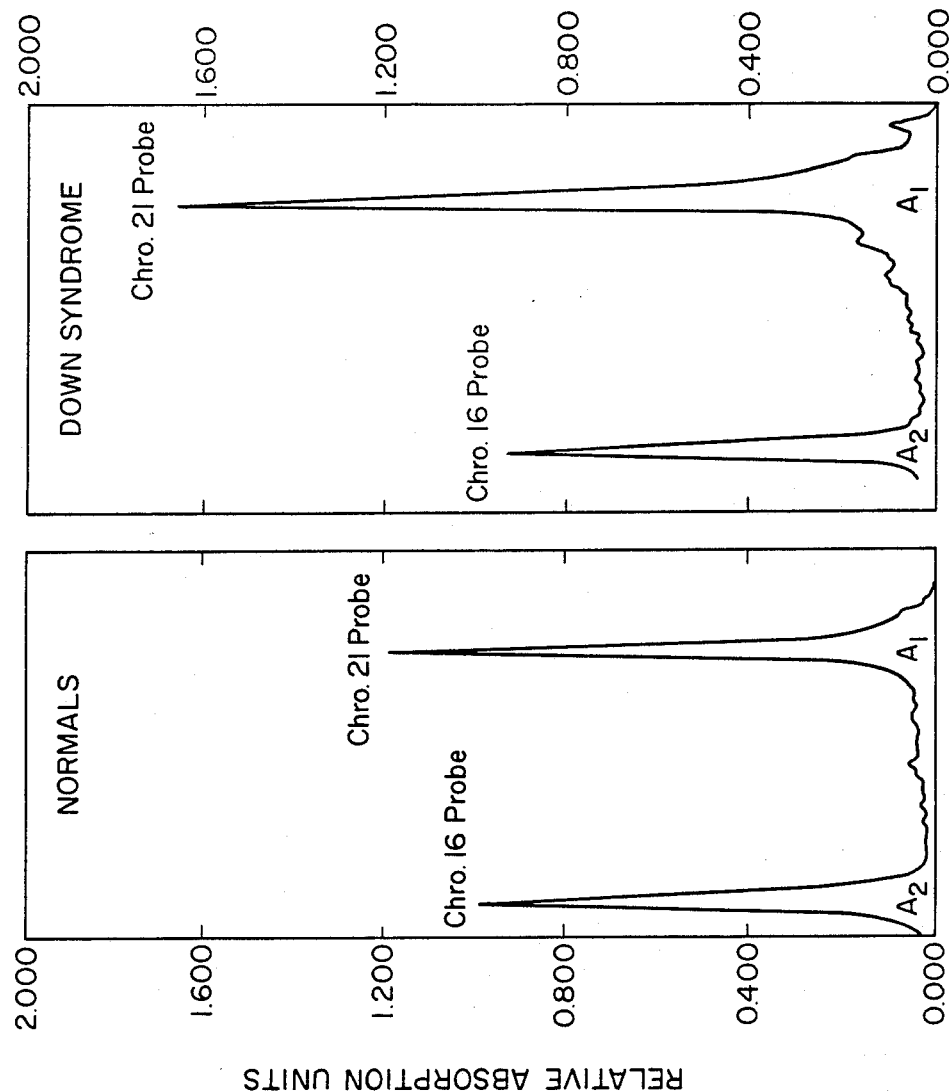
FIG. 7 is a tracing of a controlled exposure of a Southern blot of EcoRI digests of fresh leukocyte samples from Down Syndrome and non-Down Syndrome mentally retarded adults.
Figure 8:
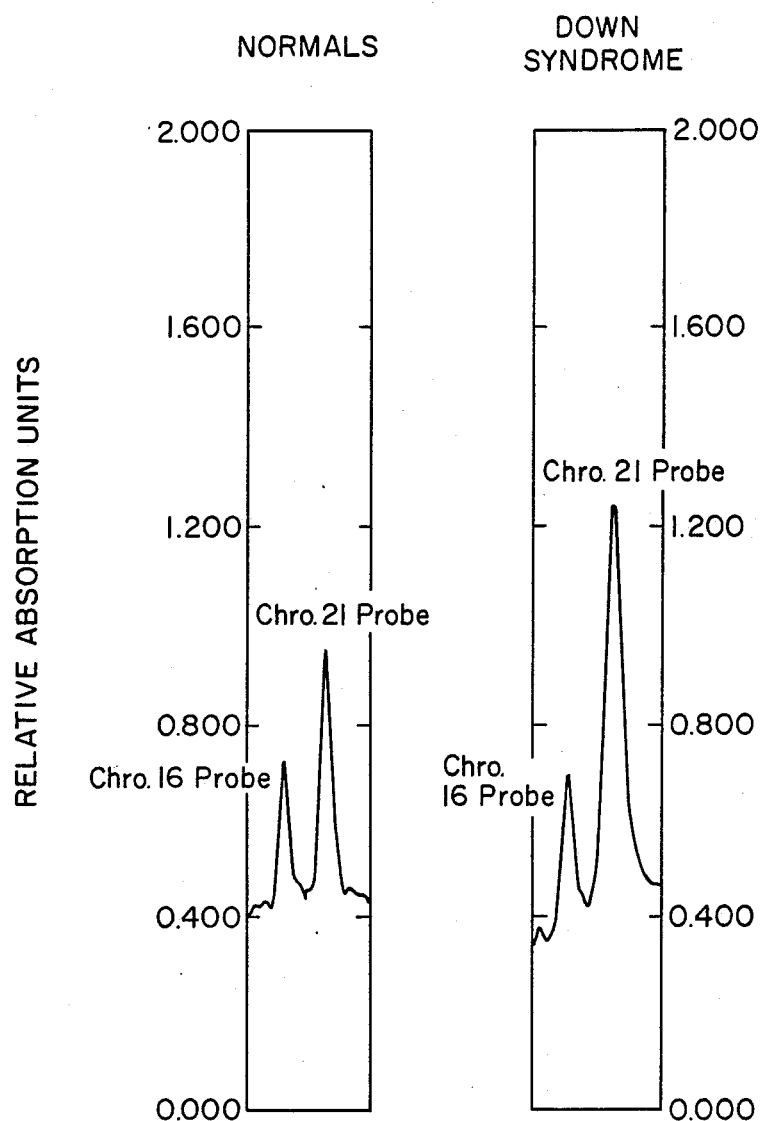
FIG. 8 is a tracing of a Hin dIII digest of Down Syndrome and normal control leukocyte samples.

Tests on leukocytes prepared from fresh blood samples from individuals clinically diagnosed as having Down Syndrome also produced discrimination among the three chromosomal types, as shown in FIG. 7 and Table II. Controls included normal and non-Down Syndrome mentally retarded adults. Different enzymes produced similar results (FIG. 8). To test the diagnostic potential of the method, coded samples were examined. Results are presented in Table III and demonstrate that successful identification occurred. Reproducibility was found with repeated tracings of the same blot, with multiple gel repeats of the same samples, and with successive DNA extractions from the same source.

TABLE I

RATIOS OF FIBROBLAST LINES

| Cell Type | $D_1/D_2$ Ideal Ratios | $A_1/A_2$ Observed Ratios | | | |
|---|---|---|---|---|---|
| monosomy 21 | 21/16 = 1/2 | 0.94 | 0.76 | 0.72 | 0.5 |
| disomy 21 | 21/16 = 2/2 | 2.08 | 1.35 | 2.64 | 1.09 |
| trisomy 21 | 21/16 = 3/2 | 3.18 | 1.78 | 4.3 | 1.72 |
| enzyme used | | Eco RI | Eco RI | Hin dIII | Hin dIII |

TABLE II

OBSERVED RATIOS OF KNOWN SAMPLES

| | | | | | | | | | |
|---|---|---|---|---|---|---|---|---|---|
| DS leukocytes | 1.24 | 1.24 | | 2.86 | 1.91 | 0.86 | 2.52 | 1.63 | 2.65 |
| DS fibroblasts | 1.3 | 1.28 | 2.46 | 2.8 | | 0.85 | | | |
| normal or non-DS retarded leukocytes | 0.4 | 0.48 | 1.7 | 1.8 | 1.05 | 0.3 | 1.23 | 0.75 | 1.37 |
| normal fibro. | | | | 1.8 | | | | | |
| normal brain | | | 1.7 | | | | | | |
| enzyme used | Eco RI | Eco RI | Hin dIII | Hin dIII | Eco RI | PST | Eco RI | Eco RI | Eco RI |

TABLE III

RATIOS OF UNKNOWN SAMPLES

| Cell Type | $D_1/D_2$ Ideal Ratios | $A_1/A_2$ Observed Ratios | | | |
|---|---|---|---|---|---|
| DS leukocytes | 21/16 = 3/2 | 2.17 | 3.38 | 2.38 | 3.25 |
| normal or non-DS retarded pers. leukocytes | 21/16 = 2/2 | 1.15 | 1.43 | 1.16 | 1.5 |
| unknowns | ? | 1.17 | 3.35 | 2.21 | 1.28 |
| diagnosis | | normal | DS | DS | normal |

Thus, results of this work demonstrate that it is possible to discriminate among varying amounts of chromosome 21. In addition to providing accurate information from individual samples, the method used provides a number of important advantages. The only requirement is that the peak heights from test and reference probes on both normal and experimental samples run on the same gel lie within the linear range of film response. Differences within lanes such as relative probe sizes, attachment efficiencies, and degrees of labelling are not important; FIG. 8 shows much lower specific activity on chromosome 16 than 21 but is still informative. Differences in loading between lanes also has no effect, because comparisons are made between internal ratios of each gel lane. This is demonstrated by the results shown in FIG. 9 for tests in which substantially different amounts of genomic DNA were used for the normal and Down Syndrome samples and yet the ability to discriminate between them was retained.

Figure 9:
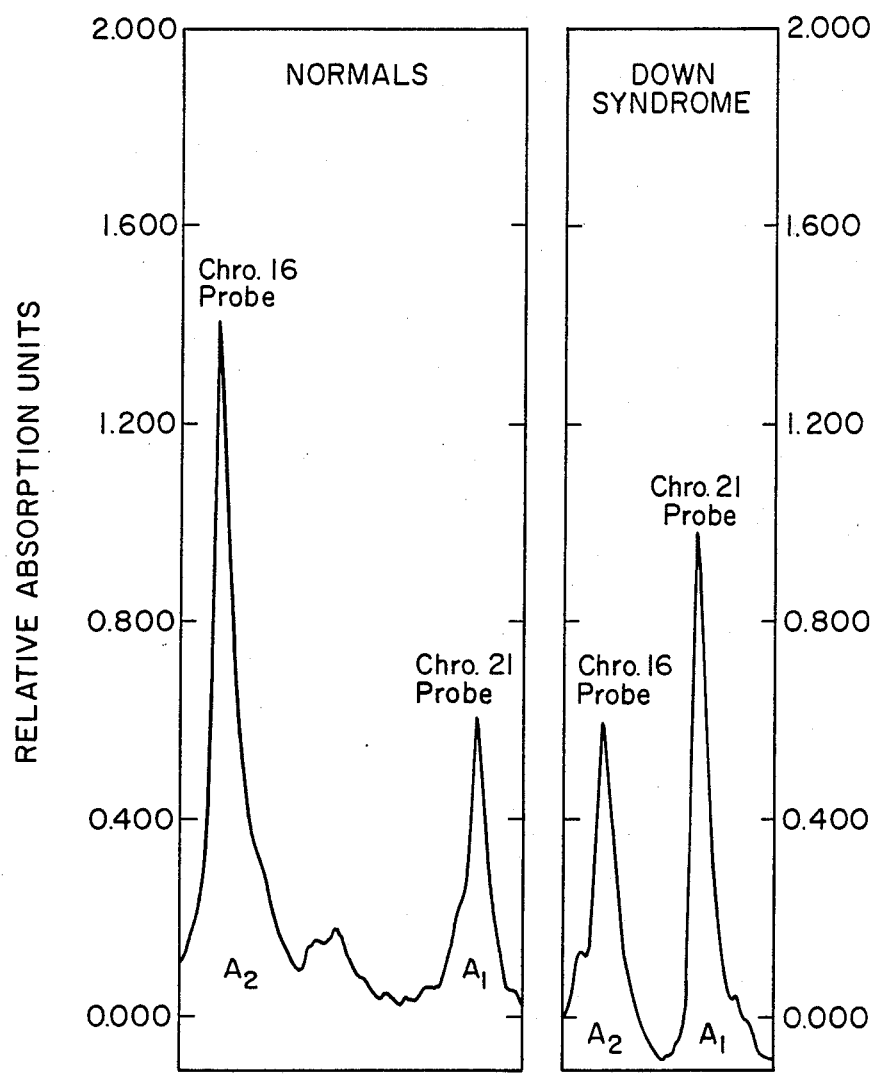
FIG. 9 is a tracing of DNA blots from disomy (normal) and Trisomy 21 (Down Syndrome) fibroblast cell lines with exposure control. The enzyme used was EcoRI.

In addition, because only area under the peaks is measured, changes of position due to restriction fragment length polymorphisms (RFLPs) are not significant if they occur outside of the homologous binding region as shown in FIG. 9 for the chromosome 21 probe. RFLPs within the homologous region can affect the area measurements. Addition of such a restriction site results in formation of two bands where one was detected otherwise: subtraction, in the elimination of one or more bands. Such occurrences are immediately obvious and can be disregarded; retesting can then be done using other enzymes. Small probe sequences minimize these possibilities.

The development of this reliable method of accurately determining changes in nucleic acid amount can serve as the basis for improved prenatal testing. Non-Trisomy 21 Down Syndrome samples are easily detected. Very early prenatal testing will be possible given that chronic villus biopsy can produce adequate DNA for blotting at four weeks of pregnancy. Williamson, R. et al., *Lancet, ii:* 1125-1127 (1981). In addition, the cost should be considerably less than that for current procedures. Because the method is extremely sensitive, it should be possible to use maternal blood, with concentration of circulating fetal cells by fluorescent activated cell sorting. Extension to testing for other chromosomal imbalances (such as Klinefelter's and Turner's Syndromes for sex chromosomes) requires only the use of different probes.

EXAMPLE II

Detection of Alterations in DNA in Samples from Alzheimer's Disease Patients

Work, as described in detail below, was carried out to determine whether differences in amount of chromosome 21 DNA can be detected in samples from the following: Alzheimer's Disease patients; persons with Down Syndrome; and normal control subjects.

In this work, the question addressed was whether the ratios for Alzheimer's Disease of chromosome 21/control chromosome would correspond to the $A_1/A_2$ value found for the 2/2 chromosome ratio for normals or the $A_1/A_2$ value found for the 3/2 for Down Syndrome individuals. For Alzheimer's Disease, each determination was made by running a normal, a Down Syndrome and an Alzheimer's Disease sample on the same gel and probing with the subclone of the gene for superoxide dismutase I (SOD) from chromosome 21 and a reference probe from chromosome 16.

A possible explanation for the development of Alzheimer's Disease assumes that triplication of a specific subsection on chromosome 21 is involved in the disease's etiology. Schweber, M., *Annals of the New York Academy of Sciences*, 450: 223-238 (1985).

Data from a number of disciplines indicates parallel effects of aging in Down Syndrome with Alzheimer's Disease. For example, all Down Syndrome adults over age 36 exhibit Alzheimer's Disease-type brain neuropathology upon autopsy. A variety of similar biochemical alterations have been found; and an epidemiological association has been reported. Balzas, R. and O. Brooksbank, *Journal of Mental Deficiency Research*, 29: 1-4 (1985). Oliver, Co. and J. Holland, *Psycholog. Med.*, 16: 307-322 (1986); Heyman, A. et al., *Annals of Neurology*, 14: 507-515 (1983); Heston, L. et. al., *Archives of General Psychology*, 38: 1085-1090 (1981). Clinically, however, most adults with Down Syndrome do not develop dementia. Ropper, A. and R. Williams, *Neurology*, 30: 639-678 (1980); Wisniewski, K. and H. Wisniewski in *Alzheimer's Disease*. B. Reisberg (Ed.), Free Press, p. 319-326 (1983). Wisniewski, K. and Rabe, *Annals of the New York Academy of Sciences*, E. Schneider (ed.), 1986. This apparent disparity between laboratory and clinical results can be reconciled by considering that the dementia of Alzheimer's Disease is expressed and defined differently for Down Syndrome persons; most of the Alzheimer's Disease initial stages involve losses of abilities which Down Syndrome adults never had. Schweber, M. In: *New Perspectives on Down Syndrome*, S. M. Pueschel et al., (ed.), pp. 135-146 (1986).

Thus, it seems reasonable to suggest that all persons with Down Syndrome develop Alzheimer's Disease with age, even though most will not exhibit gross behavioral changes. This implies that there is a unitary genetic basis for the etiology of Alzheimer's Disease and Down Syndrome. The cause of Down Syndrome is the triploid, instead of diploid, presence of a segment of chromosome 21. If all persons with Down Syndrome develop Alzheimer's Disease but not the reverse, the simplest hypothesis is that Alzheimer's Disease results from the triple presence of a minute subsection of DNA near to, or within the Down Syndrome DNA site. Such a unitary geneic hypothesis can explain the autosomal dominant genetic pattern of Alzheimer's Disease in some families (FAD) by inheritance (producing a systemic change) and its apparently sporadic appearance in others (non-FAD) by de novo formation (in somatic tissues).

Probes

Down Syndrome most commonly arises by disjunction, forming Trisomy 21. Triplication of a limited segment of chromosome 21 can also produce the phenotype. The most frequent mechanism for this is translocation. Reports of dementia and neuropathology in translocation Down Syndrome individuals suggested that if an alteration in DNA amount were involved in Alzheimer's Disease, it would be located in the vicinity of the Down Syndrome DNA. Ideally, cloned human chromosome 21 material directly from the crucial Down Syndrome DNA location would be used. This has not yet been isolated; the closest known gene is that for superoxide dismutase I (SOD). The SOD gene cytogenetically localizes to 21q22, the same chromosomal band as the Down Syndrome DNA. It produces a direct gene dosage effect in Down Syndrome (i.e., $1.5 \times$ as much enzyme is produced in Trisomy 21 individuals). Several translocations Down Syndrome persons have been identified in which SOD effects are separable from the Down Syndrome phenotype, suggesting that the Down Syndrome site(s) must be just distal to the SOD location. The cloned SOD fragment, described in Example I, was provided by Dr. Yoram Groner of the Weizmann Institute, Israel.

For control purposes, two plasmids containing fragments of the human $\epsilon$-globin gene sequence, described in Example I and obtained from Dr. Nick Proudfoot, Oxford University, England were used. No restriction mapping information was available for the SOD clone and there is only limited knowledge for the $\epsilon$-globin clones. In order to do very accurate mapping, a double digest of lambda DNA was employed, providing a full range of size markers from 23 kb to 0.4 kb. The fragments were fully calibrated with known-sized plasmids. Restriction maps were prepared using 20 enzymes. The very close correspondence of the calculated results to the expected ones in the areas of the clone whose sequence is known serve to verify the accuracy of the methods employed. None of the 20 enzymes used cut the smaller of the two $\epsilon$-globin clones, so the 1.2 kb size was employed.

Human DNA

Frozen tissues of the brains of victims of Alzheimer's Disease and other conditions were obtained from several sources. Brains were used initially because of the possibility of somatically limited alternation. Hemibrain samples were used; the other half of the sample had been fully characterized neuropathologically. Controls were age-matched brains of individuals found to have no neuropathology.

In principle, the Down Syndrome control DNA should also be obtained from brain samples. However, because of the difficulty in obtaining brain tissues from individuals having Down Syndrome, blood and fibroblasts were selected as suitable tissues. Normal blood control samples were also obtained. Blood smaples were obtained from Trisomy Down Syndrome subjects of various ages, some with karyotypic confirmation.

Isolation of DNA from the various fibroblast lines was accomplished using nuclear separation via a sucrose shelf. A simplified approach was used to isolate DNA from the blood samples. Blood samples contain mixed leukocyte and lymphoblast populations. Leukocyte purification was done. Brain DNA was prepared by extremely gentle isolation. Cesium chloride (CsCl) density gradient purification was required for Alzheimer's Disease samples with a high concentration of neuropathological structures.

Preparation of highly purified DNA from human cells in such a way that the component proportionality present in the intact genome will be maintained is an important methodological precaution (because the information to be gathered depends on testing any alteration in the disease state from the quantitative relationships of the DNA molecules present in the normal state). In addition to problems of differential extraction, there is a major methodological difficulty in obtaining purified human DNA that can be routinely and reliably digested by restriction enzymes, even using protocols that have been extensively tested. For present purposes, it is important that the DNA be reliably, easily, and reproducibly obtained in a manner that insures that no differential losses have occurred from a quantitatively representative sample of the genome involved (referred to as "good" DNA samples).

Current procedures of human DNA isolation are generally done by extraction of lysed, washed, and pelleted cells, deproteinization (using chloroform/phenol or proteinase K), ethanol precipitation, and RNA removal by RNAase with subsequent washing and dialysis. The ethanol precipitation step, involving significant losses, is sometimes omitted.

An improved isolation method was devised. An important modification from other human DNA isolation procedures is the insertion of a nuclear purification step before purification. Nuclear purification is accomplished by centrifugation of broken cells through a sucrose density shelf system, to remove cytoplasmic material before nuclei are broken open. Nuclear pellets are collected, resuspended in the lower level sucrose buffer and carefully layered over the more concentrated sucrose buffer which had been previously stabilized. Spinning through the second layer yielded a washed, purified nuclear pellet. Good results were obtained using a Hepps [4-2-hydroxy-ethyl -1-4-piperazine-propanosulfonic acid] based buffer with addition of 1.0M and 1.75M sucrose to form the two shelf stages with supplemental magnesium and calcium chelated out. Subsequent procedures followed standard methods (sarcosyl lysing, deproteinization, ethanol precipitation, enzyme treatment etc.). After extensive dialysis, final purification was performed with cesium chloride density gradient centrifugation, further dialysis, and concentration by isobutanol treatment. Tests of digestibility were performed using the enzymes Eco RI, Alu I, Hae III, Hin dIII, Hha I, Hin fII, and PST. Microscopic examination of the purified nuclear preparation showed almost 98% pure nuclei with little (or no) cytoplasmic material discernible. The final product is a purified, high molecular weight, easily digestible DNA which is assumed to have maximal conversion of the proportions of different DNA sequences present in the intact genome.

The sucrose shelf nuclear isolation was used with all fibroblast samples. Fresh samples (which we had grown) were collected, washed, and the DNA isolated as described. For frozen fibroblasts, pulverization in liquid nitrogen was done with rehydration in a hexylene glycol buffer system. After mechanical homogenization, the sucrose shelf separation was used and purification achieved with sarcosyl, phenol, chloroform/isoamyl alcohol, and extensive dialysis. For sources of material which contain relatively little cytoplasm, the use of the sucrose isolation was found to be unnecessary. Since inclusion of nuclear isolation involves less yield, a simplified system was employed for fresh blood. It was diluted into a Triton X, sucrose, Tris buffer with added magnesium. The cells were washed by repeated centrifugation, and lysis buffer added with freshly prepared proteinase K. Incubation o/n at 37° C. was done with sodium lauryl sulfate and purification achieved by phenol and chloroform/isoamyl alcohol extraction. After addition of sodium acetate, ethanol precipitation o/n at −20° C. allowed spooling out of the DNA which was then dissolved and stored.

DNA was obtained from human brains as follows. For normal individuals, the use of the sucrose shelf isolation method produced adequate DNA samples. For those clinically diagnosed as having died with AD, it is more difficult to obtain good DNA, particularly for deep frozen brain tissues. An extremely gentle method for the extraction brain DNA was developed. The samples were removed from the −80° C. conditions and immediately immersed in hydration media. The white matter was removed and the remaining tissue macerated with mechanical homogenization. Dilution and gauze filtration was followed by repeated pelleting and suspension in a sucrose-magnesium buffer. Overnight incubation was done with RNAase, sodium lauryl sulfate, and proteinase K followed by the usual phenol/chloroform: isoamyl alcohol extraction procedures and ethanol precipitation. For normal brain samples, good results could be obtained at this point. For Alzheimer's Disease samples with a high concentration of pathological structures in the brain, an additional CsCl density gradient separation seems necessary. The difference in handling requirements could reflect the presence of the very high abnormal amyloid protein concentrations in the very affected Alzheimer's Disease brains; the CsCl purification specifically removes carbohydrate moities from DNA.

Gels and Blots

Restriction mapping was done using horizontal gels. For the quantitative results, vertical rigs were used because of the greater reproducibility possible in gel thickness with such apparati. Because of the hyperbolic nature of the radioactive beta decay curve, an important parameter is the length of exposure time (i.e., only radiation deposited in the early stages of the decay process provide proportional signals).

Blots were obtained initially using Zeta TM probe paper but the advantage that it stoichastically binds to the DNA seemed to be outweighted by the difficulty in handling and reproducibility. Transfer of the DNA from the gels has been performed both mechanically and by electrotransfer device.

After hybridization of radioactively-labelled probes, films of the results were obtained, using exposure at −80° C. for varyig periods of time. Samples were tested separately with the probes from chromosome 21 and 16. The signals produced on a blot using several enzymes by the globin probe alone were then removed and the same blot hybridized to the SOD probe. This procedure permitted identification of the most appropriate enzymes to achieve separated signals from the two probes on the same sample. It was possible to find a single enzyme which would cut the genomic DNA in such a way that both probes can be used simultaneously with discrimination. As indicated, use of the 1.3kb ε-globin insert probe produces a single band with most enzymes; the 4.2kb SOD insert probe results in two bands in most cases. By judiciously comparing the sizes of the fragments, it was possible to select a single enzyme that permits distinct separation between the minimum 3 bands produced; Eco RI, Hin dIII, and PST all are usable. Differing amounts of DNA were tested to establish the most favorable conditions; the presence of only a single band was evident even at high concentrations of DNA.

Instrumentation

A new system of measuring quantitative variation in nucleic acid on blots was developed. It was important that the image of the silvered density gradient be accurately registered. This involves imposing a parallel light source for the initial imaging, as well as the production of sufficiently discrete steps so that an unequivocal densitometric tracing can be produced. The type of light source used made little difference once minimal parallelization is achieved by sufficiently distancing the source from the film. A special apparatus made to hold a high intensity strobe light was used. The frame consists of a base on which the film holder is placed, a 6 foot upright, and an arm to which the light source is attached.

For the density steps, a commercial silvered step-wedge was obtained from Kodak. It was mounted in a holder in which the X-ray film is inserted, with light-tight shielding of the unexposed portion. This allows imprinting of the image of the gradient onto one side of the film while the rest is protected. The Kodak step-wedge has the advantage of being calibrated independently and of having sufficiently broad steps. It contains 21 steps bracketing 3 O.D. units; however, the Shimadzu densitometer used measures only 2 O.D. units and its effective range is 12 steps. These are sufficient, however, since they essentially bracket 0 to 100% absorbance. It might be possible to extend this range using other equipment. Only 7 or 8 steps can be imaged on the film at one time, but, by centering the steps recorded, it is possible to fulfill the purposes of the system (i.e., insuring that measurements made will be in the linear range of response of the film).

The tracings of the image of the step-wedge gradient provide a reference frame for determining the degree of saturation of the film response. By altering the time of subsequent exposures, control of the exposure to the linear range of the film response can be achieved. Each film thus has a built-in standard reference that allows the user to adjust the exposure to the center of the linear response curve. The use of the comparative ratio of probes from two different chromosomes solves a number of other methodological problems involved in quantification of RDNA methods since all that is required is the comparison of the areas measured for both chromosomes on a single sample. For any one test, 3 genomic DNA samples are run at the same time and probed with two clones; the exposure times are controlled so that all 3 give results in the linear range with both proves. Meaningful comparisons are then possible for both diagnostic and exploratory purposes.

Use of this approach obviates many of methodological problems in RDNA methods that devolve from their very sensitivity. Because one can detect extraordinarily small amount of material with these techniques, extremely small variations in preparative or loading procedures on gels can introduce a wide range of errors. It is difficult, if not impossible, to so exactly control the loading of material on the gel that comparisons between lanes can be reliably verified. By simultaneous use of probes from two different chromosomes, all comparisons are done by densitometric tracings on single gel lanes. It is the ratio of amount of material that each probes attaches to that is significant. Any differences in the sizes of the genomic fragments from the two chromosomes to which the probes attach do not affect the readings, provided there is reproducibility between individuals in the size of the fragments generated by the enzymes used. The sizes could be affected by the presence of genetic polymorphisms provided that they reduced the fragment size, but any such result would be immediately apparent because of the alteration in the number of bands on the film.

Quantification of DNA in Samples

As stated originally, the comparison of chromosome 21 amounts to reference chromosome amounts should be 2/2 for normal cells and 3/2 for Down Syndrome cells. It is reasonable, based on the hypothesis explained above, to expect that the ratio will be 3/2 for Alzheimer's Disease cells. The ratios of 3/2 and 2/2 are the ideal. Experimentally, the results will be affected by a large number of factors. Mathematically the situation can be minimally expressed for each band as described above.

Using only the tracings of the bands on films with exposures such that the peak heights lie within the central linear part of the response curve, meaningful comparative ratios were measured on the different chromosome 21 lines. Differences in curve area for the different types of samples are apparent by eye, but must be measured.

The test of reliability has been the ability of the measured ratios to distinguish the monosomy, disomy, and Trisomy 21 cells (see Example 1). Using this criterion, no effect has been found by variation in some of the densitometric parameters; the same discrimination can be obtained with zeroing of base lines to the linear part of the wedge or to the background level. Use of a hand held planimeter permits discrimination in some of the tracings where the automated readout was unreliable. Similar discriminations are found using the planimeter or the Shimadzu automated densitometer.

Results are shown in Tables V and VI. As described in detail below, Alzheimer's Disease DNA samples were found to generate the same ratios as those of Down Syndrome samples, not those of normal controls.

Characteristics of the genomic samples used are given in Table IV. A total of 15 separate Alzheimer's Disease samples were characterized from four different tissue types. Included were six unrelated FAD cases (all with strong family patterns) and seven non-FAD patients: ten of the samples were early- and five late-onset cases. In Table I, the fibroblast samples were from siblings; both have been found to have elevated levels of SOD. The lymphoblast sample was immortalized with Epstein-Barr virus and had been obtained from an individual in whom Alzheimer's Disease occurred at age 65 (the dividing line for early and late onset). All the fresh leukocyte samples were from early onset individuals. Seven of the eight cases for which leukocytes were tested had similar clinical courses and characteristic of Down Syndrome fingerprint patterns. Cases in the group classified as sporadic had no dementia in long-lived parents, siblings, or any other relatives.

Figure 10:
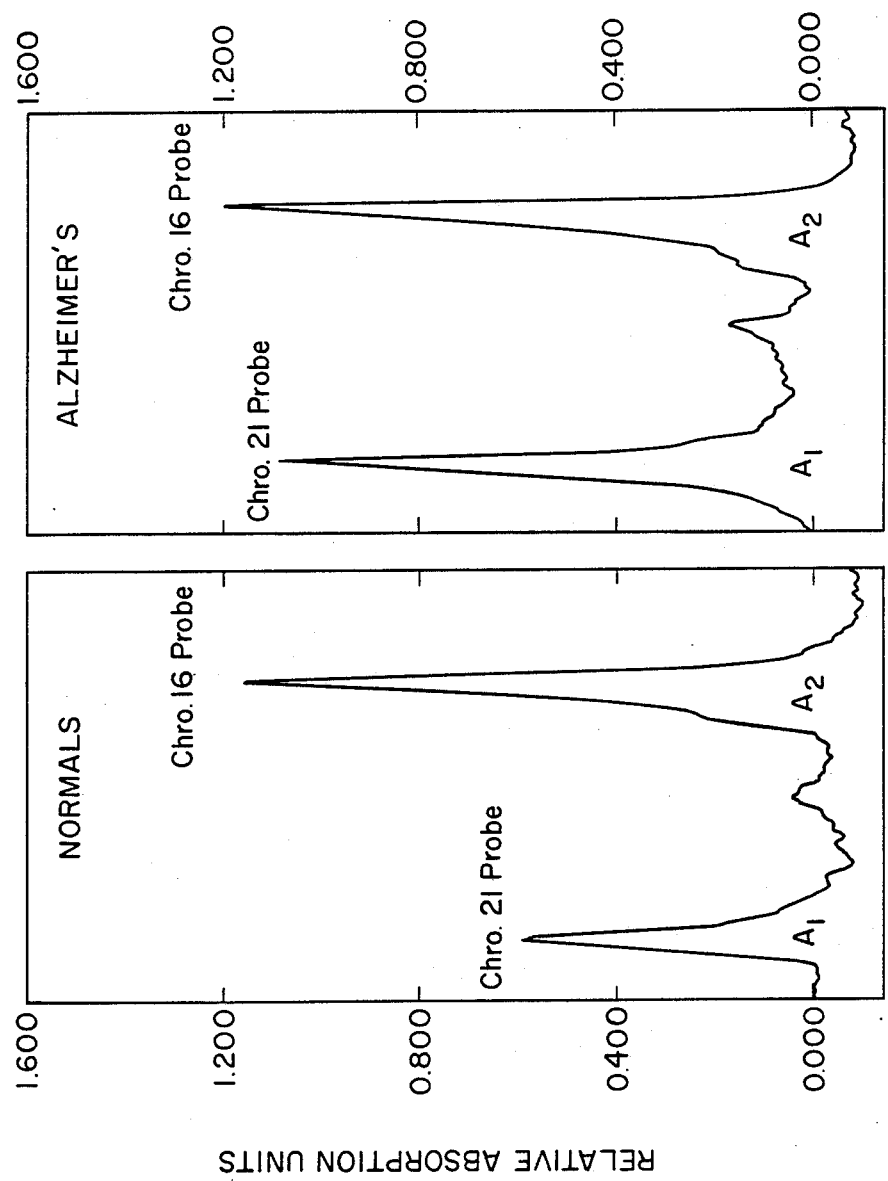
FIG. 10 is a densitometric tracing of a Southern blot of EcoRI-digested DNA from an Alzheimer's Disease brain and a normal brain, with controlled exposure.
Figure 11:
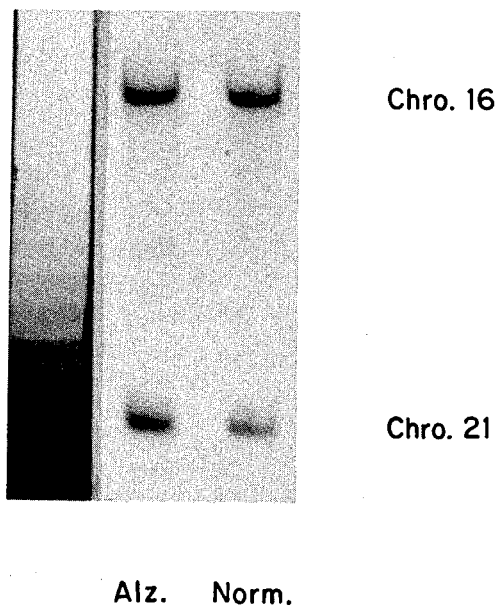
FIG. 11 is a picture of a Southern blot of EcoRI-digested DNA from an Alzheimer's Disease brain and a normal brain, with controlled exposure. The step-wedge can be oriented as seen here or across the top of the gel lanes.

Results shown in FIGS. 10 and 11 make it evident that increased amounts of chromosome 21 in Alzheimer's Disease samples are apparent by eye even before ratios are computed. Area ratios obtained with the two probes are shown in Table V and VI. Brain samples had complete neuropathology examination; age-matched normal brains were free of the neuritic plagues (NP) and neurofibrillary tangles (NFT) of Alzheimer's Disease. Using the method described above, all Alzheimer's Disease samples examined were shown, to exhibit this triplication at the SOD site. Thus, the data provide strong support for the hypothesis that there is a universal etiological basis for all Alzheimer's Disease: the triple presence of a specific region of chromosome 21.

TABLE IV

SAMPLE CHARACTERISTICS

Alzheimers Disease — AD

| Tissue Type | Age/Sex | AD Manifestiations |
|---|---|---|
| Skin Fibroblasts, #AG4401B | 53/F | Clinically FAD High SOD Levels |
| Skin Fibroblasts, #AG4402 | 47/M | Clinically FAD High SOD Levels |
| Immortalized Lymphoblasts | 80/F | Clinically FAD Autopsy Confirmation |
| Fresh Leukocytes #1 | 47/M | Clinically FAD |
| Fresh Leukocytes #2 | 59/M | Clinically FAD |
| Fresh Leukocytes #3 | 61/M | Clinically FAD |
| Fresh Leukocytes #4 | 76/M | Clinically FAD |
| Fresh Leukocytes #5 | 63/M | Clinically Sporadic AD |
| Fresh Leukocytes #6 | 66/M | Clinically Sporadic AD |
| Fresh Leukocytes #7 | 62/M | Clinically Sporadic AD |
| Fresh Leukocytes #8 | 72/M | Clinically Sporadic AD |

TABLE IV-continued

SAMPLE CHARACTERISTICS

Alzheimers Disease — AD

| | | |
|---|---|---|
| Brain Sample 1 | 68/M | Sporadic AD, High Conc. NP and NFT at Autopsy |
| Brain Sample 2 | 62/M | Sporadic AD, High Conc. NP and NFT at Autopsy |
| Brain Sample 3 | 96/M | Lowered AChE and AChAT |
| Brain Sample 4 | 75/M | Sporadic AD, Moderate Conc. NP and NFT at autopsy |

Controls

| Tissue Type | Number | Ages | Sex |
|---|---|---|---|
| Normal Leukocytes | 10 | Adults | Both |
| DS Leukocytes | 6 | 35 | Both |
| Non-DS Mentally Retarded | 3 | 35.7 | Both |
| Normal Brains | 2 | 64,60 | F,M |

TABLE V

RATIOS OF CHROMOSOME 21/16 PROBE AMOUNTS

| Tissue type | | | | | | | | | |
|---|---|---|---|---|---|---|---|---|---|
| AD Fibroblasts | | | | | 2.45 | 1.69 | | | |
| AD Brains | 1.22,1.12 | 1.37 | 2.7 | 1.91 | 2.69 | 1.67 | 1.36 | 2.80 | 2.68,2.48 |
| AD Leukocytes #1 | | | | | 2.64 | | | | |
| DS Fibroblasts | 1.21 | 1.37 | 2.8 | | | | | | |
| DS Leukocytes | 1.24 | | 2.86 | 1.91 | 2.73 | 1.72 | 1.32 | 2.52 | 2.89 |
| Normal Leukocytes | .47 | 0.5 | 1.8 | 1.05 | 1.11 | 1.09 | 0.52 | 1.23 | |
| Normal Brain | | | 1.8 | | | 1.04 | | | 1.15 |
| Monosomy Fibroblasts | | | | | 0.5 | | | | 0.44 |
| Enzyme Used | Eco R1 | Eco R1 | Hin dIII | Eco R1 | Hin dIII | Eco R1 | Hin dIII | Eco R1 | Eco R1 |

TABLE VI

RATIOS OF CHROMOSOME 21/16 PROBE AMOUNTS

| Tissue Types | A$_1$/A$_2$ Ratios | | | |
|---|---|---|---|---|
| immortalized lymphoblasts | 2.6 | | | |
| fresh leukocytes #1 | | 3.25 | | |
| fresh leukocytes #2 | | | | 2.2 |
| fresh leukocytes #3 | | | | 2.32 |
| fresh leukocytes #4 | | | | 2.43 |
| fresh leukocytes #5 | | | | 2.10 |
| fresh leukocytes #6 | | | 2.72 | |
| fresh leukocytes #7 | | | 2.77 | |
| fresh leukocytes #8 | | | | 2.27 |
| DS leukocytes | 2.56 | 3.35 | 2.69 | 2.3 |
| Normal leukocytes | 1.38 | 1.43 | 1.76 | 1.5 |

Ratios of amounts of chromosome 21 to chromosome 16 probe attachment on immortalized lymphoblasts and fresh leukocyte samples.

Triplication of DNA in Alzheimer's Disease has recently been reported for amyloid polypeptide and for the proto-oncogene ets-2, but no increase was found for the SOD locus. Delabar, J.-M. et al., *Science*, 235: 1390–1394 (1987). Possible explanations for this discrepancy from the results included here can be adduced from the nature of the SOD site and its interrelation with Down Syndrome DNA.

Figure 12:
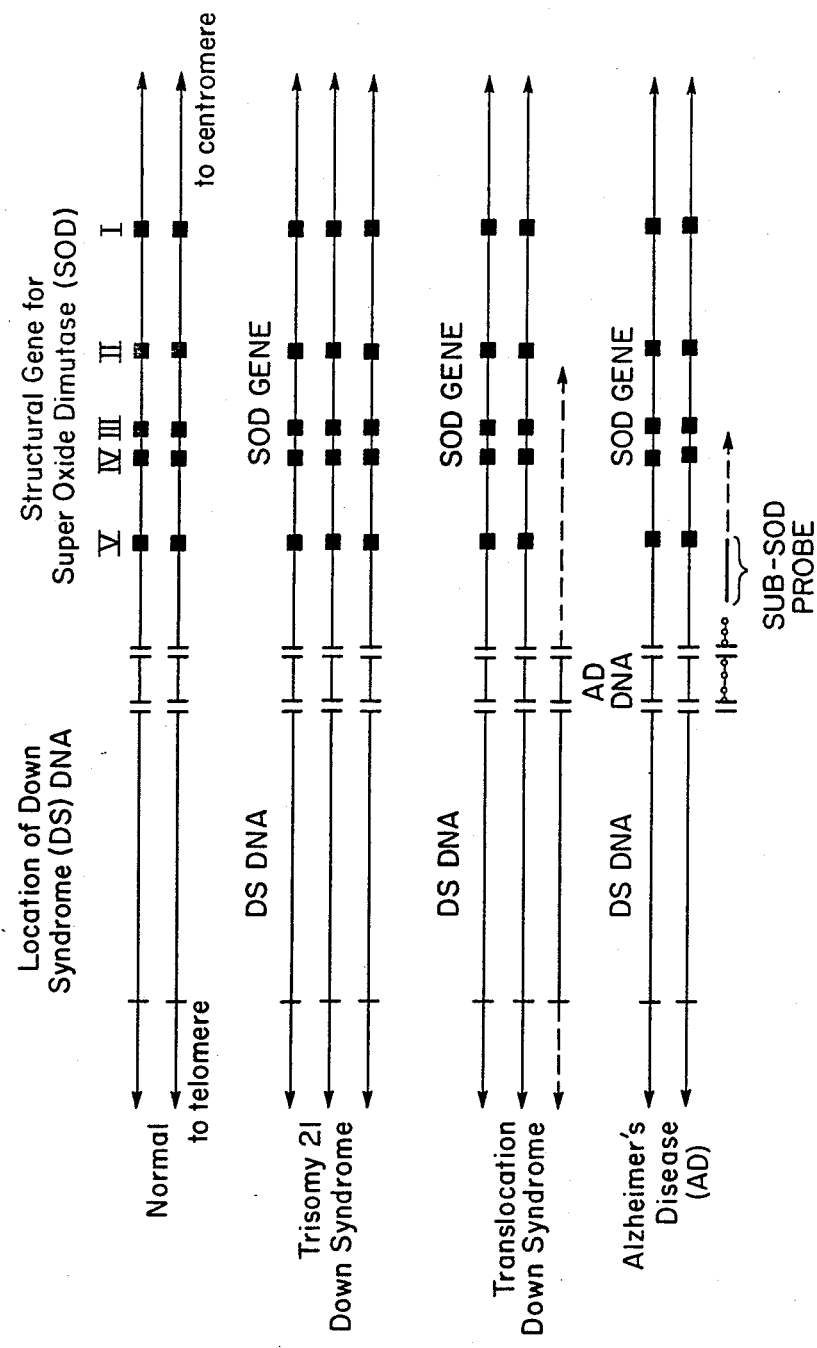
FIG. 12 presents a model of the orientation of Down Syndrome, Alzheimer's Disease and superoxide dismutase I (SOD) DNA on chromosome 21. ------indicates varying breakage sites; o-o-o-o-o-o, DNA region which is triplicated in Alzheimer's Disease.

As noted above, although most Down Syndrome is due to Trisomy 21 (FIG. 12), only limited triplication of the Down Syndrome site is required for the phenotype; usually this arises from translocations, as shown in FIG. 12. SOD DNA exhibits a gene dosage effect when tripled, producing 1.5 × the SOD gene product. Detailed karyotyping of translocations that separate the Down Syndrome and the SOD gene dosage effect suggest that the SOD locus is proximal to Down Syndrome with regard to the centromere. Some of these translocations have Down Syndrome with normal SOD levels; in these, the Down Syndrome phenotype is markedly attenuated. E. Wulfsberg et al., *Human Genetics*, 64: 271–272 (1983); Hadebank, M. and A. Rodewal, *Human Genetics*, 60: 74–77 (1982); Taysi, R., R. Sparkes, R. T. O'Brien, and D. Dengler, *J. Med. Genet.*, 10: 144–147 (1982). This could indicate a very close spatial relation of SOD and Down Syndrome DNA. Reports of translocation Down Syndrome who became demented and had full neuropathology of Alzheimer's Disease upon autopsy suggest a close spatial relation of Alzheimer's Disease with Down Syndrome DNA. Heyman, A. et al., *Annals of Neurology*, 14: 507–515 (1983); Reid, A., A. Maloney and P. Aungle, *Journal of Mental Deficiency Research*, 22: 233–241 (1978).

The SOD locus has been cloned and analyzed, establishing the organization shown in FIG. 12. Levanon, D. et al., *The EMBO Journal*, 4: 77–84 (1985). Significantly there are four pseudogenes on four chromosomes other than 21. For the work described here, a small, unique sequence subclone from the 3' end of the SOD functional strand was used, one which has no homology to any of the pseudogenes. Differing amounts of SOD product (ranging from 0 to 94% overproduction) have been found in different Alzheimer's Disease cell lines. This suggests that triplication of chromosome 21 DNA in Alzheimer's Disease is variable in extent for the SOD locus. This accumulated information combined with the results found here suggest the model for the chromosomal 21 orientation of SOD, Alzheimer's Disease and Down Syndrome DNA sequences shown in FIG. 12. The lack of triplication found at the SOD locus in Alzheimer's Disease elsewhere could result if the cloned segment employed had any homology to the pseudogenes or if it was located at the 5' end of the gene.

The model in the lowest section of FIG. 12 presents a unified, genetic model for Down Syndrome and all types of Alzheimer's Disease. Formation of the triplication in Alzheimer's Disease could occur by a variety of genetic mechanisms, including unequal crossing over, unequal sister chromatid exchange and localized DNA amplification. The basic causality of FAD and non-FAD would be the same, but with differing mechanism of acquisition. Occurrence of such an event in germ line tissues would result in FAD in subsequent generations. For non-FAD, the triplication was found in leukocytes and brains. This indicates that either germ line or somatic cell alteration is possible.

Persons with Alzheimer's Disease do not exhibit Down Syndrome characteristics, and, therefore, there is apparently some limit in extent of the triplication distally (left from the sub-SOD probe in FIG. 12). It is possible that Alzheimer's Disease persons reported to have fingerprint similarities to those of Down Syndrome have somewhat more DNA in this region. As noted, variability proximally would result in differing degrees of SOD overproduction (right from the subclone in FIG. 12).

Until the development of the method described herein, it was possible to confirm a diagnosis of Alzheimer's Disease only at post-mortem; even with improved nosological classification, clinical characterization is only 50-80% accurate. Wade, J. et al., *Archives of Neurology*, 44: 24-29, (1987); Muller, H. and G. Schwartz, *Journal of Gerontology*, 4: 504-513 (1978); Nott, P. and J. Fleminger, *Acta Psychiatr. Scand.*, 51: 210-217 (1975). The method described above makes available a laboratory diagnosis for clinically-classified FAD cases. An excellent illustration of the ability of the present method to diagnose Alzheimer's Disease is a case (included in Table IV as the third entry—Immortalized Lymphoblasts) in which the individual was clinically diagnosed as having Alzheimer's Disease, characterized as such by the method of the present invention and confirmed as such at post-mortem.

The apparently universal systemic presence of the triplication found here in all classifications of Alzheimer's Disease provides the basis for a diagnostic test. In this case, a probe specific and unique for DNA present on chromosome 21 can be used, according to the method of the present invention, to identify triplication of such DNA in individuals, as has been described above. It provides a means of laboratory confirmation of clinical diagnosis of Alzheimer's Disease, as in the case described above for the individual with immortalized lymphoblasts. It can also be used for presymptomatic identification of Alzheimer's Disease among those at risk. This technique also has application in prenatal diagnosis of familial Alzheimer's Disease. For example, DNA in sufficient quantity can be obtained, e.g., by trophoblastic excision of a chorionic villus (or villi, if necessary) or from maternal blood. The method described herein can be applied to detect the occurrence of triplication of DNA on chromosome 21. In individuals belonging to families in which Alzheimer's Disease occurs (familial Alzheimer's Disease) or in whom the disease has been clinically diagnosed, determination that triplication of the chromosome 21 DNA is present will be strongly indicative of the presence of Alzheimer's DNA (DNA associated with the occurrence of Alzheimer's Disease). Establishment of a specific triplication as the necessary causative prerequisite of Alzheimer's Disease will provide a framework for new therapeutic strategies.

Equivalents

Those skilled in the art will recognize, or be able to ascertain using no more than routine experimentation, many equivalents to the specific embodiments of the invention described herein. Such equivalents are intended to be encompassed by the following claims.

I claim:
1. A method of assuring linearity of densitometric measurement relative to exposure of a film, comprising the steps of:
   a. providing a film having a density reference image on a limited region, the reference having a range of densities;
   b. exposing a separate region of the film to form an image which provides the basis of the densitometric measurement;
   c. performing a densitometer measurement of the film; and
   d. determining whether the density range of the separate region image lies within a range of densities which are within the linear range of response of the film as defined in the densitometer tracing of the reference image.

2. A method as claimed in claim 1 wherein the densitometer reference is a gradient of incremented density steps.

3. A method as claimed in claim 1 wherein the separate region of the film is exposed by radioactively-identified biological molecules.

4. A method as claimed in claim 3 wherein the density gradient is preimaged using a visible light source.

5. A method as claimed in claim 3 wherein the linear range of response of the film can be identified by imposing the images of a series of concentrations of a radioactive source on a separate region of the film using a standard source of radiation.

6. A method of assuring linearity of densitometric measurements of biological molecules relative to exposure of a film, comprising the steps of:
   a. treating biological molecules to produce fragments;
   b. spatially orienting the fragments according to size;
   c. attaching radioactively labeled probes to identify specific fragments;
   d. providing a film having a density reference image on a limited region, the reference having a range of densities;
   e. exposing a region of the film separate from the limited region having a density reference image thereon to the radioactively-labeled probes attached to spatially-oriented fragments, to form an image on the film;
   f. developing the film;
   g. performing a densitometric tracing of the density reference image and of the image formed by exposure of the film to the spatially-oriented, radioactively-labeled probes attached to the fragments; and
   h. determining whether the densitometric tracing produced by exposure to the image resulting from exposure to the fragments lies within the linear range of response of the film, as defined by the densitometric tracing of the density reference image.

7. A method as claimed in claim 6 wherein the biological molecules are nucleic acids which are treated by digestion with appropriately selected restriction site endonucleases to produce fragments and the fragments are radioactively identified by hybridization with specific, radioactively-labeled probes comprising a nucleic acid sequence homologous to the nucleic acid sequence of the fragments of interest.

8. A method of assuring linearity of densitometric measurements of DNA relative to exposure of a film, comprising the steps of:
   a. isolating DNA from a sample;
   b. treating isolated DNA to produce DNA fragments;
   c. spatially orienting fragments according to size;
   d. radioactively identifying DNA fragments by hybridization with a specific, radioactively-labeled probe comprising a nucleic acid sequence homologous to the nucleic acid sequence of the DNA fragments of interest;
   e. providing a film having a density reference image on a limited region, the reference having a range of densities;
   f. exposing a region of the film separate from the limited region of the radioactively-identified, spatially-oriented DNA fragments, to form an image on the film;
   g. developing the film;
   h. performing a densitometric tracing of the densitometric reference image and of the image formed by exposure to the spatially-oriented, radioactively-identified DNA fragments; and
   i. determining whether the densitometric tracing produced by exposure to the DNA fragments lies within the linear range of response of the film, as defined by the densitometric tracing of the reference image.

* * * * *